US010774313B2

(12) United States Patent
Joshi

(10) Patent No.: US 10,774,313 B2
(45) Date of Patent: Sep. 15, 2020

(54) TWO PLASMID MAMMALIAN EXPRESSION SYSTEM

(71) Applicant: Vishwas Joshi, Maharashtra (IN)

(72) Inventor: Vishwas Joshi, Maharashtra (IN)

( * ) Notice: Subject to any disclaimer, the term of this patent is extended or adjusted under 35 U.S.C. 154(b) by 620 days.

(21) Appl. No.: 15/229,308

(22) Filed: Aug. 5, 2016

(65) Prior Publication Data

US 2017/0029786 A1 Feb. 2, 2017

Related U.S. Application Data

(62) Division of application No. 14/124,383, filed as application No. PCT/IN2012/000405 on Jun. 8, 2012, now Pat. No. 9,441,205.

(30) Foreign Application Priority Data

Jun. 8, 2011 (IN) ........................ 1679/MUM/2011

(51) Int. Cl.
| | |
|---|---|
| *C12N 15/85* | (2006.01) |
| *C12N 7/00* | (2006.01) |
| *C12N 15/86* | (2006.01) |
| *A61K 39/00* | (2006.01) |

(52) U.S. Cl.

CPC ............... *C12N 7/00* (2013.01); *C12N 15/85* (2013.01); *C12N 15/86* (2013.01); *A61K 39/00* (2013.01); *C12N 2760/00051* (2013.01); *C12N 2760/18451* (2013.01); *C12N 2800/40* (2013.01); *C12N 2840/203* (2013.01)

(58) Field of Classification Search
None
See application file for complete search history.

(56) References Cited

U.S. PATENT DOCUMENTS

| | | | | |
|---|---|---|---|---|
| 5,716,821 | A | 2/1998 | Wertz et al. | |
| 2008/0274130 | A1 | 11/2008 | Rupprecht et al. | |
| 2009/0017517 | A1* | 1/2009 | Schickli ................... | C12N 7/00 435/173.6 |
| 2010/0028377 | A1 | 2/2010 | Jin et al. | |

FOREIGN PATENT DOCUMENTS

| | | |
|---|---|---|
| WO | WO 97/06270 | 2/1997 |
| WO | WO 98/13501 | 4/1998 |
| WO | WO 00/26517 | 5/2000 |
| WO | WO 2004/113517 A2 | 12/2004 |

OTHER PUBLICATIONS

Martin et al., "RNA Polymerase II-Controlled Expression of Antigenomic RNA Enhances the Rescue Efficacies of Two Different Members of the *Mononegavirales* Independently of the Site of Viral Genome Replication," Journal of Virology, Jun. 2006, vol. 80, No. 12, 5708-5715.

Groseth et al., "RNA Polymerase I-Driven Minigenome System for Ebola Viruses," Journal of Virology, Apr. 2005, vol. 79, No. 7, 4425-4433.

Yanai et al., "Development of a novel Borna disease virus reverse genetics system using RNA polymerase II promoter and SV40 nuclear import signal," Microbes and Infection 8 (2006) 1522-1529.

Finke et al., "Differential Transcription Attenuation of Rabies Virus Genes by Intergenic Regions: Generation of Recombinant Viruses Overexpressing the Polymerase Gene," Journal of Virology, Aug. 2000, vol. 74, No. 16, 7261-7269.

Szymczak et al., "Development of 2A peptide-based strategies in the design of multicistronic vectors," Expert Opinion Biol. Ther. (2005) 5(5) 627-638.

Szymczak et al., "Correction of multi-gene deficiency in vivo using a single 'self-cleaving' 2A peptide-based retroviral vector," Nature Biotechnology vol. 22, No. 5, May 2004, 589-594.

Huang et al., "Development of a reverse genetics system for a human rabies virus vaccine strain employed in China," Virus Research 149 (2010) 28-35.

Parida et al., "Rescue of a chimeric rinderpest virus with the nucleocapsid protein derived from peste-des-petits-ruminants virus: use as a marker vaccine," Journal of General Virology (2007), 88, 2019-2027.

Bailey et al., "Reverse genetics for peste-des-petits-ruminants virus (PPRV): Promoter and protein specificities," Virus Research 126 (2007) 250-255.

Raha et al., "Development of a reconstitution system for Rinderpest virus RNA synthesis in vitro," Virus Research 99 (2004) 131-138.

Radcliffe et al., "Multiple gene products from a single vector: 'self-cleaving' 2A peptides," Gene Therapy (2004) 11, 1673-1674.

Supplementary European Search Report and Written Opinion issued in EP 12 83 5226 dated Jan. 14, 2015 (10 pages).

International Search Report issued in PCT/IN2012/000405 dated Mar. 4, 2013 (4 pages).

* cited by examiner

*Primary Examiner* — Mindy G Brown

(74) *Attorney, Agent, or Firm* — RatnerPrestia

(57) ABSTRACT

Described is a simple plasma-based mammalian expression system that uses the RNA dependent RNA polymerase (RDRP) enzyme systems' activity for expression of recombinant proteins or RNA from viral minigenomes and rescue of recombinant viruses from cDNAs encoding entire genome(s) of negative stranded RNA viruses for use in synthesizing recombinant viruses and developing vaccines. This system will be used for expression of recombinant proteins, therapeutic RNA molecules including anti-sense and/or selecting interfering RNA and Ribozymes. This system can also be used for gene therapy and producing recombinant viruses for production of new vaccines.

5 Claims, 16 Drawing Sheets

Specification includes a Sequence Listing.

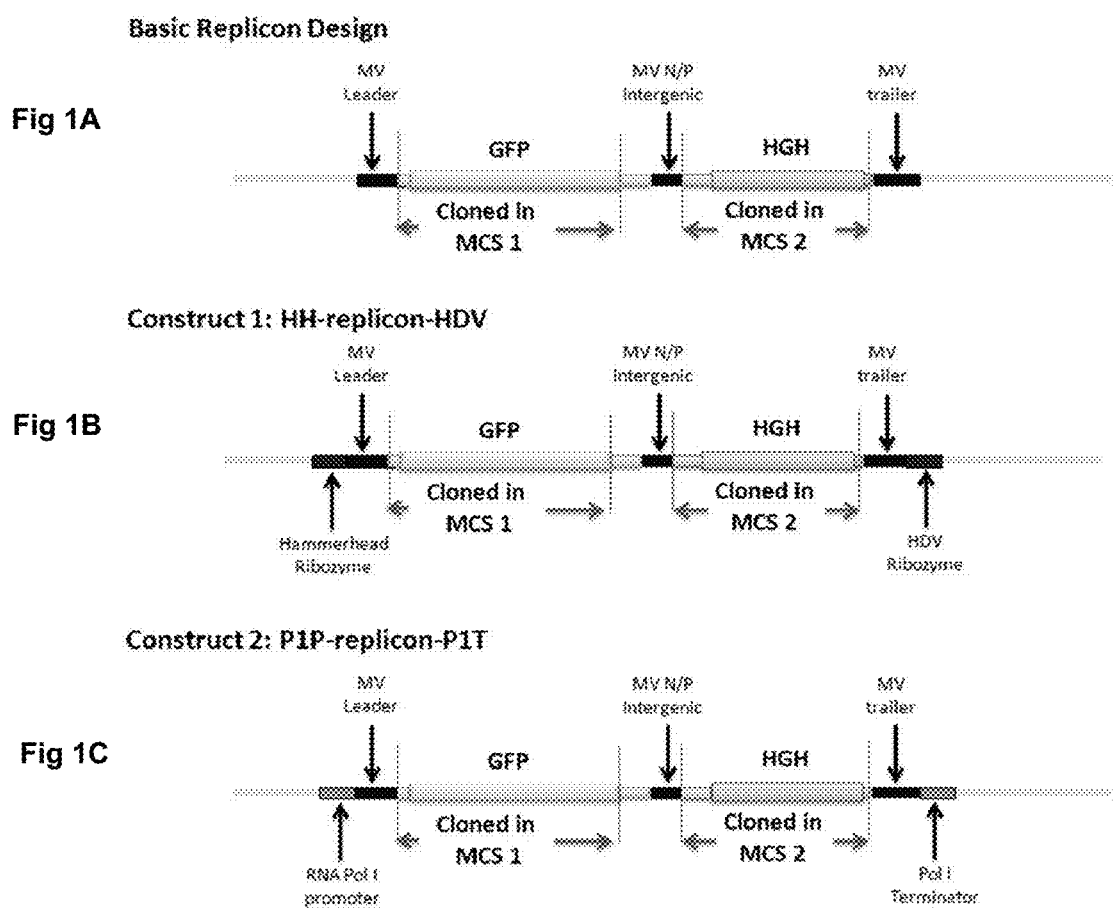

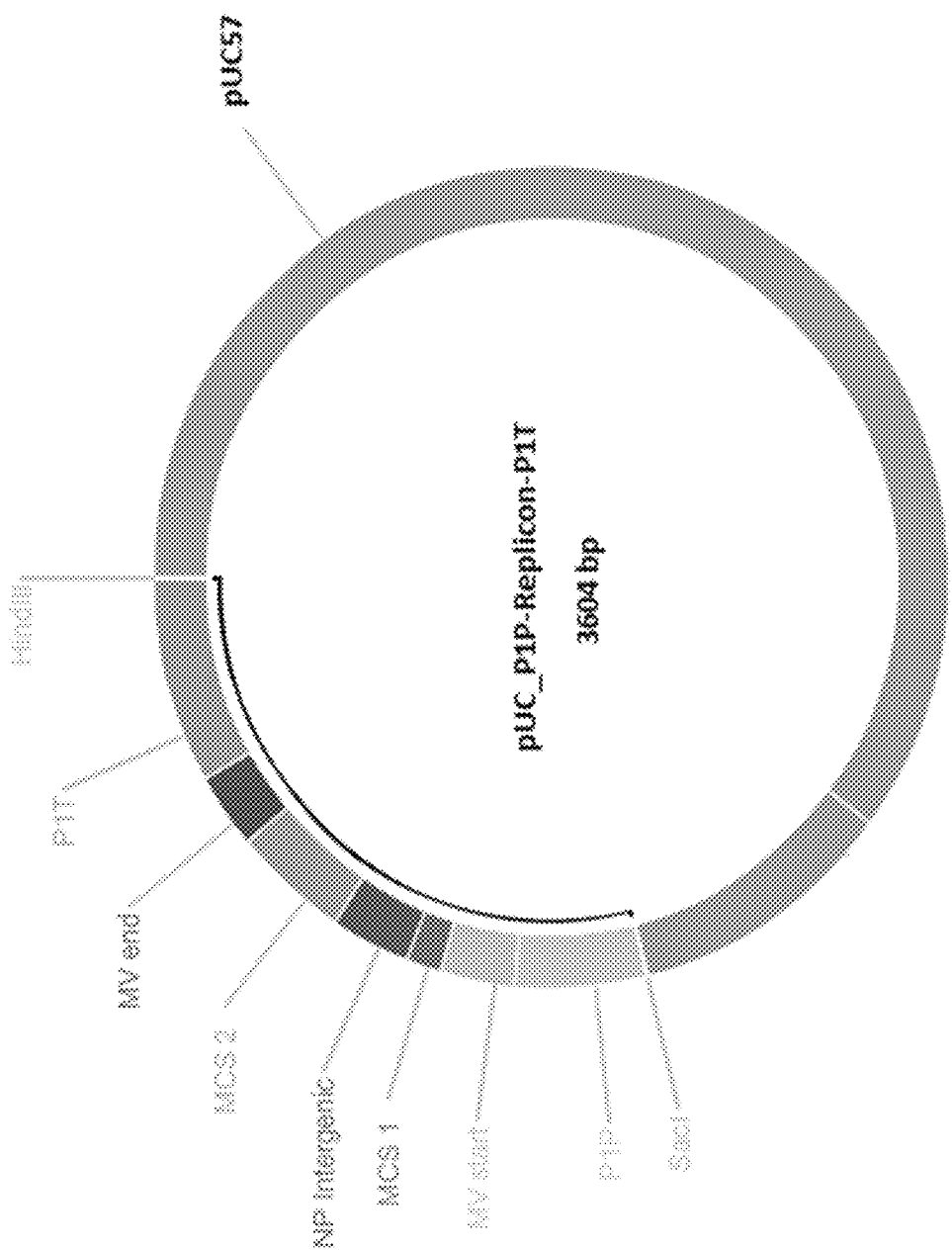
Fig 2A cloning plasmid 1

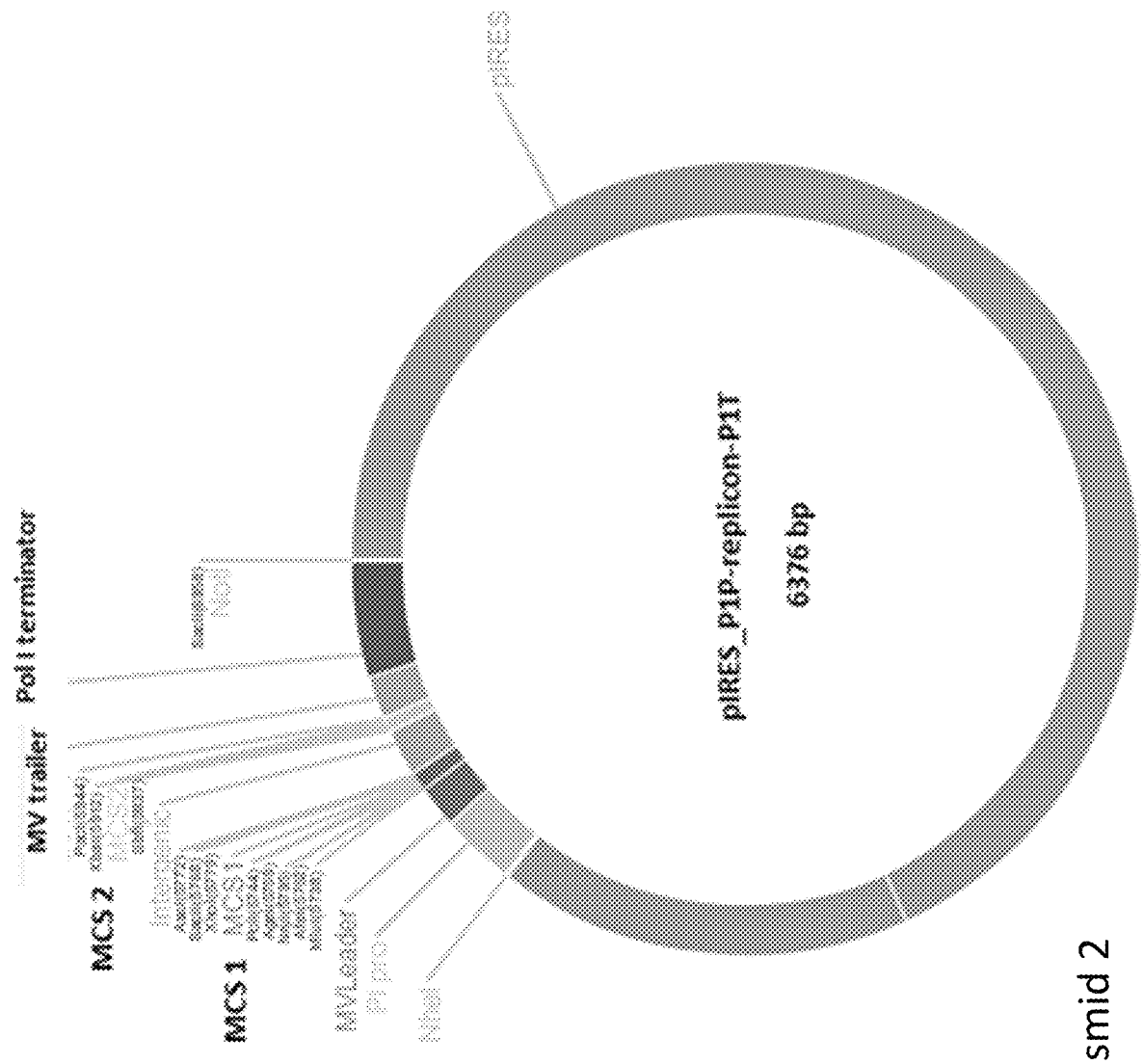
Fig 2B cloning plasmid 2

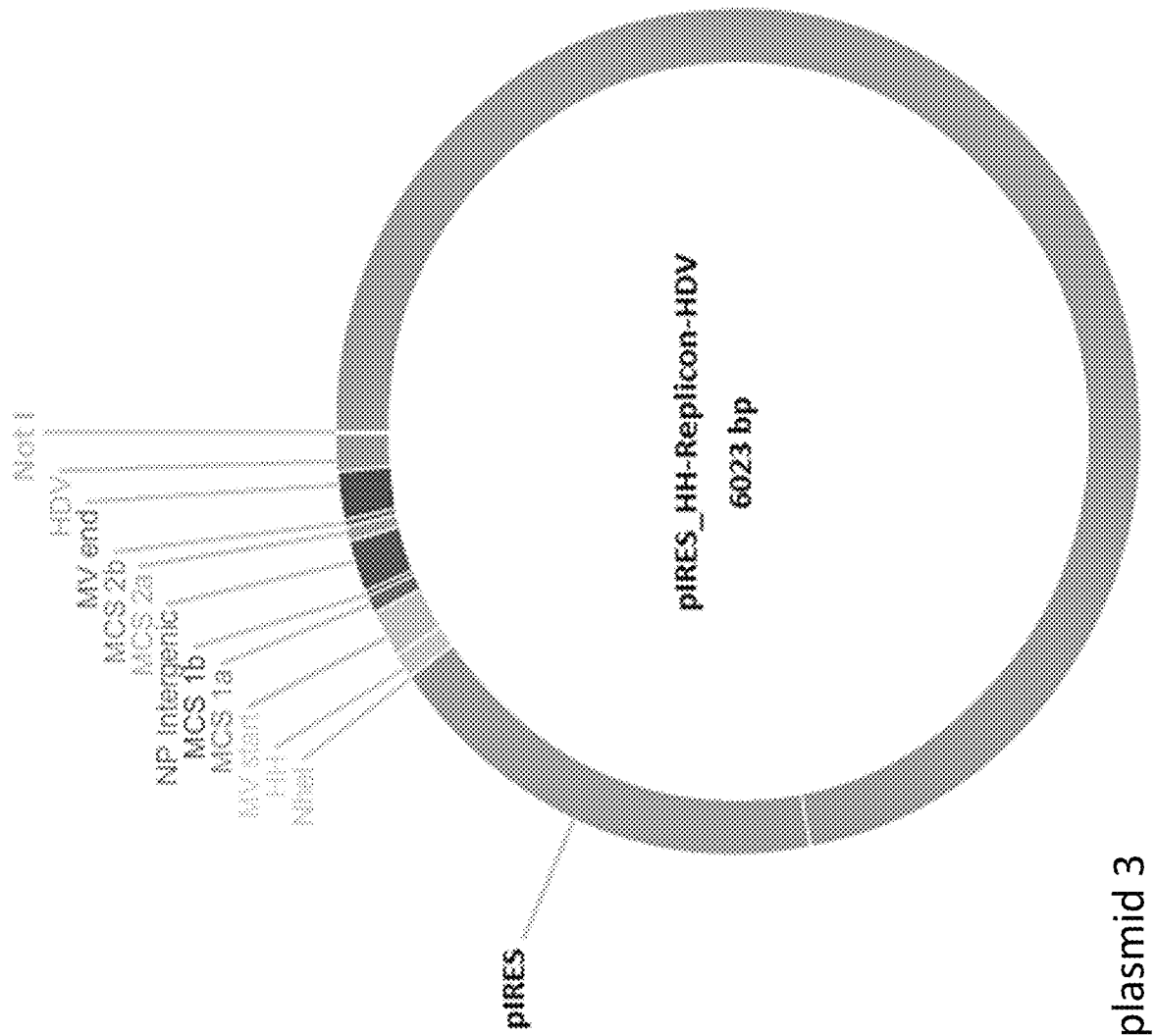
Fig 2C cloning plasmid 3

TWO PLASMID MAMMALIAN EXPRESSION SYSTEM

CROSS REFERENCE TO RELATED APPLICATIONS

This application is a U.S. Divisional Application of U.S. patent application Ser. No. 14/124,383, filed Feb. 27, 2014, now U.S. Pat. No. 9,441,205, which issued Sep. 13, 2016, which is the U.S. National Phase Application of PCT/IN2012/000405, filed Jun. 8, 2012, which claims priority to Indian Patent Application No. 1679/MUM/2011, filed Jun. 8, 2011, the contents of such applications being incorporated by reference herein.

FIELD OF INVENTION

The present invention relates to a two plasmid mammalian expression system. Moreover invention relates to production of recombinant proteins and viruses. Moreover the present invention relates to a mammalian expression system incorporating methodology for reconstitution of Ribonucleic acid (RNA) dependent RNA polymerase enzyme of negative stranded RNA viruses and its exploitation as a mammalian expression system for the production of proteins, RNA molecules and recombinant viruses.

BACKGROUND OF INVENTION

Advances in molecular biology and genetic engineering led to the development of "Reverse Genetics", a process of generating recombinant viruses from a cloned complimentary DNA (cDNA) copy of a viral genome. It has helped understand the molecular determinants related to virus attenuation, tissue tropism virulence factors and in recent years, accelerated the development of virus vaccines by enabling easy modification of viral genomes through manipulation of its cDNA. Reverse genetics has made it possible to produce recombinant viruses with attenuating mutations or chimeric viruses expressing heterologous genes for use as new viral vaccines or therapeutic agents.
Morbilli Viruses (Measles Virus and Rinderpest Virus)

MV and RPV are members of the genus morbillivirus of family Paramyxoviridae. Their genetic information is encoded on a single stranded RNA genome of antisense polarity and comprises 15894 (MV) and 15882 (RPV) nucleotides respectively. Their genome has unique highly conserved 3' and 5' termini called leader and trailer respectively and encodes 6 genes—N (nucleocapsid protein), P (phosphoprotein), M (matrix protein), F (fusion protein), H (hemagglutinin) and L (large protein=polymerase)—separated by similarly conserved intergenic sequences. In infected cells, viral RNA dependent RNA polymerase (RDRP) initiates transcription of genomic RNA from its promoter present within the leader sequence and produces messenger ribonucleic acid (mRNA) molecules which are translated into corresponding proteins by the cellular ribosomes. At some point in the viral lifecycle and after adequate pools of viral proteins are synthesized, the RDRP enzyme switches mode and initiates replication from another promoter present within the leader sequence of the genomic RNA. Although the exact mechanism(s) regulating the initiation of transcription or replication of viral RNA and transcription start and stop at gene boundaries is poorly understood, the conserved sequences which serve as promoters for transcription and replication and sequences which dictate the transcription start and end at each gene boundary are clearly defined in case of most negative stranded RNA viruses in general and MV and RPV in particular. It is well established that addition of these sequences to any unrelated RNA molecule forms a "virus genome like replicon" which can be transcribed and replicated by its cognate RDRP.

MV causes an acute febrile illness in infants and young children. Its prevalence can be controlled very effectively by vaccination. Most of the currently used live attenuated vaccines including the Schwartz, Moraten, and Edmonston-Zagreb strains are derived from the original Edmonston strain (Enders and Peebles, 1954) by multiple passages in non human cells (Enders, 1962). However, according to the estimates of the World Health Organisation (WHO), one million young children die every year from measles mainly in developing countries. But in recent years developed countries such as the USA with incomplete adherence to vaccination have seen emergence of measles related deaths (Clements and Cutts, 1995). For a recent discussion of MV vaccinology including future trends see Norrby (1995). During the past 60 odd years, Measles vaccine has been administered in over 700 million children and has proved to be highly effective, usually providing life-long immunity against MV reinfection.

RPV causes cattle plague—an infectious viral disease of cattle, buffalo and other wild life species and is mainly India, Africa and other tropical countries. It is characterized by fever, oral erosions, diarrhea, lymphoid necrosis and high mortality. Two vaccines—Plowright (Plowright and Ferris, 1962) and Lapinized (Scot 1963) have been widely used to protect against rinderpest. The Plowright vaccine derived by attenuation of RBOK strain of RPV has proved to be most effective (Baron et al, 2005). Wide spread use of these vaccines helped irradicate RPV from several countries including India by 2000. However, its reemergence in 2003 has led to resumption of mass vaccinations of cattle and other susceptible animals (Kock et al, 2006).

The proven safety and efficacy of these vaccines, supports their use as an ideal vector for the expression of heterologous genes. Reverse genetics offers a powerful approach for developing recombinant MV or RPV useful as potential vaccines against unrelated diseases and/or therapeutic agents in man and animals.

Reverse genetics was first used to generate RNA viruses by Racaniello and Baltimore in 1981 in case of Poliovirus. Subsequently, several other positive-sense RNA viruses were generated using synthetic RNA produced by T7 or T3 RNA polymerase (Racaniello, V. R. & Baltimore, D., 1981) from a cloned cDNA. Generation of negative stranded RNA viruses however, proved more difficult. Unlike positive stranded RNA viruses, the genome of negative sense viruses cannot be translated by host cells and is not infectious. It must be supplied in the form of ribonucleoprotein (RNP) complexes containing the nucleoprotein and the viral RDRP proteins to allow its transcription and replication and subsequent virus formation. Enami et al, (1990) developed the first reverse genetics system to produce influenza virus (which consists of 9 genomic RNA subunits). Its RNPs are small in size and can be assembled in vitro from RNA and required viral proteins—N and the polymerase components. Initially an artificial RNA carrying a reporter gene—chloramphenicol acetyl transferase (CAT) sequence embedded in viral non-coding terminal sequences of the influenza virus genome subunit was used (Luytjes et al., 1989). Later, single authentic or altered genome subunit RNAs transcribed in vitro from cloned DNA were also used (Enami and Palese, 1991). The assembled RNPs replicated and transcribed upon transfection into influenza-infected cells, as monitored by CAT production and by rescue of a influenza virus, respectively. Purification of virus containing the introduced subunit from the vast excess of non-reassorted virus in some cases can be accomplished by selection, for example, using a specific neutralising antibody directed against the protein encoded by the cognate subunit of the helper virus.

The RNPs of nonsegmented negative-strand RNA viruses (Mononegavirales) contains in addition to N protein, the assembly and polymerase cofactor phosphoprotein (P) and the viral RNA polymerase (large protein L) and are more difficult to assemble in vitro from synthetic RNA and individual proteins. Therefore, many researchers preferred to use smaller subgenomic RNAs (viral minigenomes) containing the essential sequences of viral genome produced during virus lifecycle were used. They were then substituted by artificially transcribed RNA molecules from DNA constructs containing reporter genes and viral essential non-coding sequences (replicons). Replication of such replicons carrying the CAT coding sequence and viral noncoding terminal sequences was achieved for Sendai virus (Park et al., 1991), Sendai virus (SeV), respiratory syncytial virus (Collins et al., 1993; Collins et al., 1991), human parainfluenza virus 3 (Dimock and Collins, 1993), rabies virus (RV) (Conzelmann and Schnell, 1994) and MV (Sidhu et al., 1995).

A similar system was used to rescue vesicular stomatitis virus (VSV) (Lawson et al., 1995; Schnell, et al, 1994) and rabies virus (RV) entirely from a full length cDNA clone of viral genome under the control T7 RNA polymerase promoter. The components of the viral polymerase complex including the nucleoprotein (NP) were provided from protein expression plasmids that were controlled by T7 RNA polymerase promoter. Soon other researchers also reported generation of non-segmented negative-sense RNA viruses from cloned genomic cDNA for vesicular stomatitis virus (Whelan, et al, 1995), measles virus (Radecke et al, 1995), respiratory syncytial virus (Collins, et al, 1995), sendai virus (Garcin, et al, 1995; Kato et al, 1996), rinderpest virus (Baron & Barrett 1997), human parainfluenza virus (Hoffman et al, 1997; Durbin et al, 1997), simian virus (He et al, 1997), newcastle disease virus (Peeters, et al, 1999) and human severe acute respiratory syndrome corona virus (Yount, et al, 2003).

These demonstrations and other studies of reconstitution of RNA dependent RNA polymerase (RDRP) enzyme activity and its ability to rescue corresponding RNA viruses or non-viral reporter proteins from minireplicons have establish the RDRP enzyme as a powerful versatile system for expression of recombinant proteins either alone or as integral parts of rescued viruses.

The most common methodology used for this purpose, uses transfection of multiple plasmids—one expressing the substrate RNA (a cDNA encoding viral genome or an artificial replicon) and others expressing the viral RDRP complex proteins—viz. the nucleocapsid (N or NP protein), the phosphoprotein (P) and the large polymerase (L) protein and an external T7 RNA polymerase (T7RNAP) to allow expression from these plasmids. The T7 RNAP is used for multiple reasons—(1) its high efficiency, (2) its ability to synthesize RNA with correct 5' terminus identical to viral genome and (3) its ability to transcribe DNA molecules within the cytoplasm thus eliminating modifications of vRNA by RNA splicing, polyadenylation or other mechanisms.

T7RNAP is not a mammalian enzyme. Therefore Pattnaik et al, (1990) used a recombinant attenuated vaccinia virus (VV) (e.g. MVA/T7). It was used for recovery of VSV (Lawson et al, 1995) and rabies virus (Conzelman, U.S. Pat. No. 6,033,886), RSV (Collins et al, 1995), the SV5 (He et al, 1997), HPIV-3 (Durbin et al, 1997), rinderpest virus (Barn and Barrett 1997) and measles virus (Schneider et al, 1997), mumps virus (Clarke et al, 2000), CDV (Gassen et al, 2000), HPIV-2 (Kawano et al, 2001) and BPIV-3 (Schmidt et al, 2000). Similarly, a recombinant fowlpox virus expressing T7RNAP has also been used to supply T7RNAP for recovery of newcastle virus (NDV) (Peeters et al. 1999) and of a chimeric rinderpest virus (Das et al. 2000).

The recombinant viruses produced using this approach are mixed with vaccinia virus and are difficult to purify which can be a major problem—especially if the recombinant viruses are required for preparing immunogenic compositions or gene therapy vectors. Moreover, this helper vaccinia virus kills the host cells limiting the efficiency of recombinant virus production. Therefore, it would be desirable to eliminate the use of helper virus supplying T7 RNA polymerase. Three different approaches have been used to eliminate the use of externally supplied T7RNAP altogether.

Radecke et al, (1995) produced a helper cell line constitutively expressing T7RNAP and Measles virus (MV) N and P proteins (WO 97/06270) and introduction of a plasmid encoding the entire (+) strand sequence of MV genome linked to T7RNAP promoter and another plasmid encoding MV L protein alone is sufficient to rescue recombinant MV. However, the efficiency of this helper cell line is usually limited and requires to be enhanced by giving a heat shock (Parks et al, 1999). Also, this cell line is only useful for rescue of MV. In contrast, the helper BHK-21 cell line (BSR T7/5) stably expresses only the T7RNAP and can be used for rescue of different viruses as shown in case of BRSV (Buchholz et al. 2000), rabies virus (Finke and Conzelmann 1999), VSV (Harty et al. 2001), NDV (Romer-Oberdorfer et al. 1999), and Ebola virus (Volchkov et al. 2001). It can be used to reconstitute RDRP of any virus by co-transfecting with plasmids encoding appropriate N, P and L proteins.

Second approach involves the use of RNA polymerase I (RNAPI). RNAPI is usually involved in transcription of ribosomal genes in mammalian cells. The RNAs synthesized by RNAPI do not contain the 5' methyl cap structure and 3' poly-A tail. The transcription initiation and termination signals for RNAPI are precisely defined and RNA molecules produced by inserting viral genomic or genome like cDNA molecules in between rRNA promoter and terminator signals possess authentic viral 5' and 3' ends, does not require further processing and can be used as a substrate directly by viral RDRP if expressed. (Zobel et al, 1993, Nucleic acids research, 21:3607-3612; Flick and Petterson, 2001, J. Virol. 75: 1643-1655;). Therefore, RNAPI transcription has been used to synthesize viral genomic or genomic like cDNA from plasmids and used for rescue of viruses in case of Influenza virus (Neumann et al, 1999), Borna disease virus and MV (Martin et al, 2006, J Virol. 80:5708-5715).

More recently, Martin et al, (2006) have used a third strategy to express viral genomic RNA from transcripts produced by RNA polymerase II (RNAP II). They placed a hammerhead ribozyme immediately upstream of and a genomic hepatitis delta virus ribozyme immediately downstream of the virus genomic sequence. These ribozymes cleaved a genomic RNA with authentic 3' and 5' ends from the RNA transcribed by RNAP II.

Such strategies eliminate the need for helper virus but still require separate helper plasmids expressing the viral N, P and L proteins. Transfection of so many plasmids simultaneously in a cell and ensuring useful levels of expression of the desired proteins for efficient reconstitution of RDRP can be difficult. Availability of a single helper plasmid expressing all desired genes will help increase the efficiency of virus rescue by ensuring that all transfected cells will receive the entire complement of helper proteins necessary for reconstitution of RDRP enzyme activity.

This requirement for multiple plasmids has also restricted the use of RDRP based systems to virus rescue, where as studies with artificial replicons encoding reporter proteins has shown that RDRP mediated expression systems can allow high levels expression of recombinant proteins. Availability of a single helper plasmid/reagent to supply the required N, P and L proteins will help expand the scope of using RDRP enzyme for large scale expression of recombinant proteins. Therefore, there exists a need in the art for new simpler methods and reagents which will allow efficient reconstitution of RDRP activity and its exploitation for expression of recombinant proteins, RNA molecules and/or rescue of recombinant viruses.

Here, we describe the preparation and use of simple easily manipulatable plasmid vector systems which can be used for reconstitution of RDRP enzyme activity and its rescue for expression of recombinant proteins, RNA molecules and rescue of recombinant viruses. For this purpose, we have used the RDRP system of 2 viruses—Measles virus (MV) and Rinderpest virus (RPV) as models. These plasmids can be easily modified to express either non-viral proteins, RNA molecules or the entire viral genomes. This vector system will be useful in development of applications related to protein expression and/or generation of recombinant modified viruses (virus rescue) expressing additional proteins and/or RNA molecules useful for vaccination or other therapeutic purposes.

OBJECT OF THE INVENTION

An aspect of the present invention provides a two plasmid mammalian expression system for production of recombinant proteins and viruses Another aspect provides a method for reconstitution of RNA dependent RNA polymerase and its exploitation as a mammalian expression system.

A further aspect of the inventions provides a mammalian expression system for the expression of recombinant proteins, nucleic acid, viruses, RNA molecules.

Still a further aspect of the invention provides a mammalian expression system for the intracellular expression of RNA molecules like aptamers, antisense RNA, miRNA, siRNA, ribozymes etc Yet another aspect of the invention provides reagents for production of recombinant viruses useful as vaccines or therapeutic agents.

Another aspect of the invention describes the process of the preparation of such a mammalian expression system.

SUMMARY

The present invention features the use of RNA dependent RNA polymerase enzyme of morbilliviruses for expression of proteins, RNA molecules and production of recombinant viruses in mammalian cells. In one aspect this provides a plasmid DNA molecules which expresse the N, P and L proteins of MV. In another aspect of this invention, it provides another plasmid which expresses easily manipulatable RNA substrate of RDRP which can be used for production of any protein, RNA or modified virus. These plasmids may be used as a reagent kit for expression of proteins or RNA molecules or production of recombinant viruses or combination thereof. Further this invention provides a method for using these plasmids for intracellular expression of RNA molecules which may be useful for modulation of cellular gene expression. These plasmids may be used in the form of cloning kits.

The following terms/abbreviations used in the specification have meanings attributed to them as mentioned hereinbelow.

MV: Measles Virus, RPV: Rinder Pest Virus, RNA: Ribonucleic acid, DNA: Deoxyribonucleic acid, RDRP: RNA Dependent RNA Polymerase, cDNA: Complimentary DNA, -VRNA: Negative sense Viral RNA, RNP: Ribonucleoprotein, P: Phospho Proteins, L: Large Polymerase Proteins, N: Nucleocapsid, CMV:Cytomegalovirus, IRES: Internal Ribosomal Entry Site, CHO Cell Line: Chinese Hamster Ovary Cell Line, RNA Pol I-RNA Polymerase I, MOI: Multiplicity of Infection, siRNA: selective interfering RNA, miRNA: micro RNA, GFP: green fluorescent protein, HGH: human growth hormone

BRIEF DESCRIPTION OF THE DRAWING

FIGS. 1A-1C: Schematic diagrams of the cloning plasmids encoding the Measles Minireplicon encoding 2 reporter genes.

FIG. 1A: Basic replicon Design

FIG. 1B: Construct 1: HH-replicon-HDV

FIG. 1C: Construct 2: P1P-replicon-P1T

FIGS. 2A-2C: Schematic representations of the Cloning Plasmids created.

FIG. 2A: Cloning Plasmid 1: Vector pUC57 was used to clone P1P_Replicon_P1T construct.

FIG. 2B: Cloning plasmid 2: Vector pIRES was used to prepare pIRES_P1P_Replicon_P1T construct.

FIG. 2C: Cloning plasmid 3: Vector pIRES was used to prepare pIRES_HH_Replicon_HDV.

FIG. 3A: Generation of cDNA encoding the entire antigenome of MV-E: Viral RNA was purified using Genejet RNA purification kit (Fermentas) and reverse transcribed using Superscript II and random hexamer primers. This was used to amplify seven overlapping fragments with Superscript III and specific primers and cloned into pCDNA3.1 in which the multiple cloning site was replaced with a Nhe I_Not I_Pac I_Pme I linker.

FIG. 3B: Plasmid encoding cDNA of MV-E genome: cDNA encoding entire antigenome of MV-E was synthesized by assembling seven overlapping PCR amplified fragments and cloned in Not I and Pme I sites of pCDNA 3.1(−)

FIG. 4A: Helper Plasmid 1: Vector pBiCMV-1 was used to prepare pBiCMV_MV-N_MV-P_IRES_MV-L.

FIG. 4B: Helper plasmid 2: Vector pIRES was used to prepare pIRES_MV-N_p2A_MV-P_MV-L.

FIG. 5A: Vero cells were co-transfected with Cloning plasmid encoding eGFP and HGH and HPV1 or HPV 2, incubated for 48 hrs at 37° C. and observed for fluorescence and HGH. A: pUC 18 alone;

FIG. 5B: pGFP (positive control);

FIG. 5C: pUC_P1P-replicon-P1T alone;

FIG. 5D: pUC-P1P-replicon-P1T and Helper HPV;

FIG. 5E: pIRES-HH-replicon-HDV alone;

FIG. 5F: pIRES-HH-replicon-HDV and HPV. Note: Helper plasmids 1 and 2 both were able to supply the N, P and L proteins. Representative pictures of HPV1 alone are shown as they were similar.

FIG. 6A: Vero cells transfected with pUC-P1P-rep-P1T, pCDNA-MVgenome & Helper plasmid variant 1;

FIG. 6B: Vero cells transfected with pIRES-HH-rep-HDV, pCDNA-MVgenome & Helper plasmid variant 1.

DETAILED DESCRIPTION AND EXAMPLES

Figure 3A:
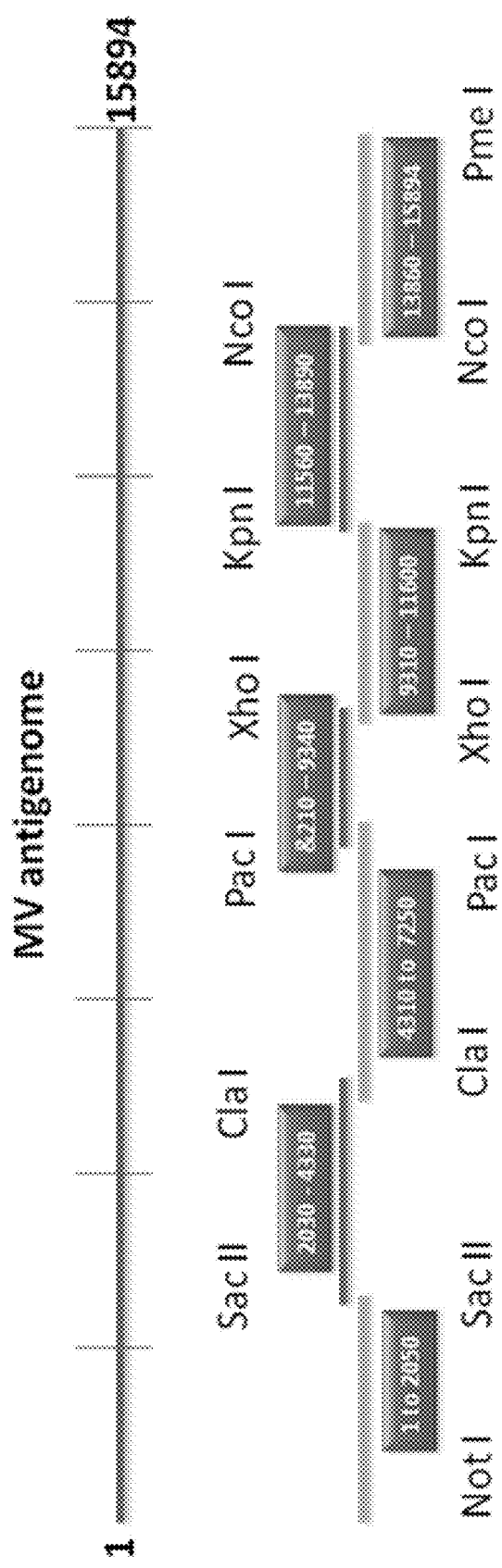
FIGS. 3A-3B: Synthesis of cDNA of entire MV-E genome

The present invention relates to expression system that can be easily used for cellular reconstruction of the RDRP enzyme activity for the expression of recombinant proteins or virus rescue. It comprises of two plasmids—1. helper plasmid which expresses N, P and L proteins of MV virus and 2. a Cloning Plasmid which expresses easily manipulatable viral RNA or viral like RNA molecule (minireplicon). The cloning plasmid contains multiple cloning sites (MCS) for easy insertion of DNA encoding target molecule to be expressed. Here MV and RPV are used as model system.

EXAMPLES

The invention will be further described in the following examples, which do not limit the scope of the invention described in the claims.

1. Cells and Viruses

Vero (African green monkey kidney) cells were grown as monolayers in Dulbecco\'s modified Eagle\'s medium (DMEM) supplemented with 5% fetal calf serum (FCS). MRC5 cells were grown as monolayers in DMEM supplemented with 10% FCS. Measles virus (Edmonston) (MV-E) strain was purchased from Serum Institute of India (MVAC, $10^3$ TCID50/vial). To prepare a seed stock, Vero or MRC5 cells were seeded in 25 sq. cm flasks at $10^5$ cells/flask and incubated for 36 hrs. Cells were then washed with HBSS and seeded with MV-E at a MOI of 0.1 and supplemented with serum free DMEM. Virus was harvested at 24 hr intervals. Virus collected over 72 hrs was pooled together, quantitated and used as seed stock.

2. Plasmid Constructions 2.1 Cloning Plasmid 2.1.1 Designing the Replicon Construct The MV leader (ntds 1 to 107), MV trailer (ntds 15786 to 15894) and the intergenic region between the protein coding regions for MV-N and MV-P proteins (ntd. No 1686 to 1806) were selected from the AY 486084.1 sequence from Genbank (Baricevic et al, 2005). Coding regions for the green fluorescence protein (eGFP) and human growth hormone (HGH) to be used as reporter proteins were isolated from U55762.1 and NM-000515.3 respectively. All these sequences were assembled in silico into a MV-E genome like replicon containing 2 gene cassettes. Nucleotide sequences corresponding to recognition sites for Afe I, Age I, Asc I, Mlu I, Nru I, Pci I, Sac II, Xho I, Eco RI, Pac I, Pme I, Pml I, Sbf I and Xba I were arranged into 2 oligonucleotides to synthesize 2 multiple cloning sites (MCS1 and MCS 2) and inserted in the replicon around the EGFP and HGH genes. As a result, the EGFP protein appeared to have been cloned within the MCS1 region at Asc I site and HGH protein within MCS 2 at Pac I site (FIG. 1A). The sequence of the replicon without the reporter genes is given in Seq ID No. 1.

The sequence corresponding to a 5' hammer head ribozyme was reconstructed from Combredet et al, (2003) and attached at the 5' end of the replicon. Similarly, sequence for 3' hepatitis delta virus ribozyme was adopted from Walker et al, (2003) and appended at the 3' end of replicon to generate a HH-replicon-HDV construct (FIG. 1B; Seq ID No. 2).

Sequences encoding the promoter for chinese hamster RNA polymerase I (P1P) was selected from Tower et al, (1989) and a terminator sequence for murine RNA polymerase I terminator (P1T) was selected on basis sequences described by Grummt et al, (1985, 1986). The P1P sequence was added at immediately upstream of the 5' terminus (immediately upstream) and P1T sequence was appended immediately downstream of the 3' terminus of replicon to create P1P-replicon-P1T construct (FIG. 1C; Seq ID No. 3).

2.1.2 Synthesis of Cloning Plasmids

Sequences corresponding to the HH-replicon-HDV (between Eco RI & Hind III sites) and P1P-replicon-P1T (between Sac I and Hind III sites) were synthesized using the gene synthesis method of Young and Dong (2004) and cloned into pUC57 to create pUC_HH-replicon-HDV and pUC_P1P-replicon-P1T (FIG. 2A—Cloning plasmid no. 1) respectively. They were then subcloned in between Nhe I and Not I sites of pIRES vector from Clonetech to generate pIRES_HH-replicon-HDV (FIG. 2C—Cloning plasmid no. 3) and pIRES_P1P-replicon-P1T (FIG. 2B—Cloning plasmid no. 2) plasmids. These plasmids were used for testing the RNA dependent RNA polymerase (RDRP) mediated expression of GFP and HGH proteins in mammalian cells.

After confirming that these plasmids expressed GFP and HGH under the control of RDRP, the genes for EGFP and HGH were removed by sequential digestion and ligation with Asc I and Pac I to create 3 variants of cloning plasmids—Cloning Plasmid variant 1 (HH-replicon-HDV) and Cloning plasmid variant 2 (P1P-replicon-P1T) and Cloning Plasmid Variant 3 (pUC_P1P-replicon-P1T). The different plasmids created are listed in Table 1.

TABLE 1

Different Minireplicon plasmids created.

| No | Name | Description | Sequence No |
|---|---|---|---|
| 1 | Cloning plasmid 1 (pUC-P1P-Rep-P1T) | Replicon under the control of CHO cellular RNA polymerase I promoter and murine RNA polymerase I terminator in pUC57 without reporter genes | Seq ID No. 6 |

TABLE 1-continued

Different Minireplicon plasmids created.

| No | Name | Description | Sequence No |
|---|---|---|---|
| 2 | pUC-HH-Rep-HDV | Replicon flanked by Hammerhead and Hepatitis Delta virus ribozymes at the 5' and 3' termini and cloned in pUC57 vector without reporter genes | Seq ID No. 7 |
| 3 | Cloning plasmid 2 (pIRES-P1P-Rep-P1T) | Replicon under the control of CHO cellular RNA polymerase I promoter and murine RNA polymerase I terminator subcloned into the Nhe I and Not I sites of pIRES vector from Clonetech without reporter genes | Seq ID No. 5 |
| 4 | Cloning plasmid 3 (pIRES-HH-Rep-HDV) | Replicon flanked by Hammerhead and Hepatitis Delta virus ribozymes at the 5' and 3' termini subcloned into the Nhe I and Not I sites of pIRES vector from Clonetech without reporter genes | Seq ID No. 4 |
| 5 | Cloning Plasmid 1 with reporter genes | Replicon containing reporter genes eGFP and HGH under the control of CHO cellular RNA Polymerase I promoter and murine RNA polymerase I terminator cloned in pUC57 | |
| 6 | Cloning Plasmid 2 with reporter genes | Replicon containing reporter genes eGFP and HGH under the control of CHO cellular RNA Polymerase I promoter and murine RNA polymerase I terminator subcloned into Nhe I and Not I sites of pIRES vector from Clonetech. | Seq No. 32 |
| 7 | Cloning Plasmid 3 with reporter genes | Replicon containing reporter genes eGFP and HGH flanked by Hammerhead and Hepatitis Delta virus ribozymes at the 5' and 3' termini subcloned into the Nhe I and Not I sites of pIRES vector from Clonetech | Seq No. 33 |

2.1.3 Synthesis of cDNA of Entire MV-E Genome

The MV-E cDNA was cloned from viral particles purified from a batch of MV-E vaccinepurchased from the Serum Institute of India, Pune, India. Viral RNA was extracted from $10^5$ lysed virus particles using GeneJet RNA purification kit (Fermentas) according to the manufacturer's RNA purification kit according to the manufacturer's protocol. The viral RNA was reverse transcribed into cDNA using random hexamers and Superscript II DNA polymerase. As Seven overlapping cDNA fragments covering the entire viral genome (as shown in FIG. 3a) were generated by PCR using PfuTurbo DNA polymerase and the following primers (1)
5'-GCGGCCGCACCAAAC-3';

(2)
5'-CCTGACCGCGGATGC-3';

(3)
5'-ACCTCGCATCCGCGG-3';

(4)
5'-CCTCCAGAGTAATCGATTAAGG-3';

(5)
5'-AATCGATTACTCTGGAGGAGCAG-3';

(6)
5'-CTTGCACCCTAAGTTTTAATTAACTAC-3';

(7)
5'-GAACAATATCGGTAGTTAATTAAAAC-3';

(8)
5'-TGAGGGACTCGAGCATACTC-3';

(9)
5'-ATAAGATAGTAGCCATCCTGGAGTAT-3';

(10)
5'-GTAGGGCCATGTGCTGGG-3';

(11)
5'-CATAGCCGTAACAAAAAGGGTAC-3';

(12)
5'-GAGCATCAAGTGAAGGACCATG-3';

(13)
5'-GCATTGTGGTATTATAGAGCCTATC-3';

(14)
5'-CGGTTTAAACCAGACAAAGCTG-3'

Figure 3B:
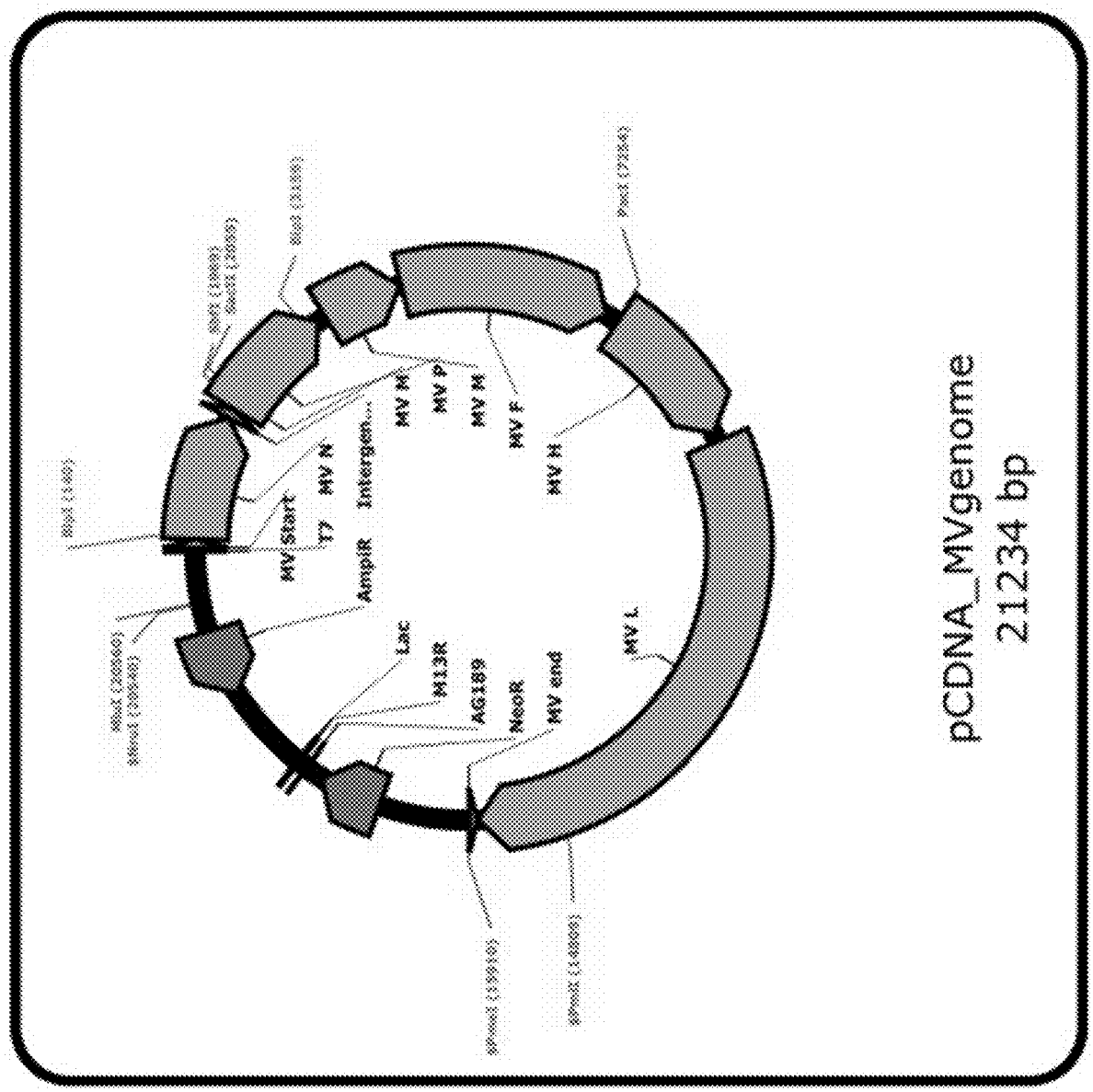

The multiple cloning site from the plasmid pCDNA3.1(−) was removed by digestion with Nhe I and Pme I and replaced it with a linker containing Nhe I-Not I-Pac I-Pme I sites pCDNA-Not_Pac_Pme. The fragments generated by using different primer pairs 7, 8 (Pac I, Xho I), 9,10 (Xho I, Kpn I), 11,12 (Kpn I, Nco I) and 13, 14 (Nco I, Pme I) and ligated into a Pac I-Pme I digested pCDNA-Not_Pac_Pme to generate a plasmid with the nucleotides from Pac I to the 3' end of the MV-E antigenome called pCDNA_Not_Pac_MVg_Pme. The fragments generated by other three pairs— 1,2 (Not I, Sac II), 3, 4 (Sac II, Cla II), 5, 6 (Cla I, Pac I) were ligated into the Not I-Pac I digested pCDNA_Not_Pac_MVg_Pme plasmid to create pCDNA_MVgenome (FIG. 3b).

2.2 Helper Plasmid

RNA was prepared from the purified MV-E virus purchased from Serum Institute of India, Pune, India using the GeneJet RNA purification kit (Fermentas) according to the manufacturer's protocol. 1 µg RNA was reverse transcribed using random hexamers and amplified using primers specific for the N (F: 5'-GCTAGCATGGCCACACTTTTAAGG-3' and R 5'-GCGGCCGCCTAGTCTAGAAGATT-3'), P (F 5'-GCTAGCATGGCAGAAGAGCAGG-3',R 5'-GCGGC-CGCCTACTTCATTATTATC-3') and L (F 5-GCTAG- CATGGACTCGCTATCTGTCAAC-3, R 5-GCGGCCGCT-TAGTCCTTAATCAG-3) protein coding regions using Superscript III (Invitrogen) as described by Martin et al, (2006) and Combredet et al (2003) using standard molecular cloning techniques. Amplified cDNAs were cloned in between the Nhe I and Not I sites of pIRES vector (Clonetech) to generate pIRES_N, pIRES_P and pIRES_L plasmids.

2.2.1 Synthesis of Helper Plasmid Variant 1

N protein gene was amplified from pIRES_N and subcloned into Eco RI and Pst I sites of pBiCMV1 to generate pBiCMV_N plasmid. The P protein sequence was then amplified and cloned in Nhe I and Eag I sites to create the pBiCMV_NP construct. The L protein sequence was then subcloned in the Eag I and Sal I sites of pBiCMV_NP plasmid to generate pBiCMV_NPL plasmid. This plasmid contains a bidirectional CMV promoter and can express the N and P proteins. However, the L sequence will be transcribed as a bicistronic RNA with P and will not be translated. Therefore, a mammalian beta globin IRES element (ires) described first by Chappell et al, (2000) and later on confirmed by Touzlet et al, (2008) to promote efficient translation was inserted immediately upstream of L coding region. An oligonucleotide encoding a pentameric IRES element flanked by a site for Eag I at 5' end and the first 10 nucleotides of L protein at 3' end (5' GGCCGTTCTG ACATCCGGCG GGTTTCTGAC ATCCGGCGGG TTTCTGACAT CCGGCGGGTT TCTGACATCC GGCGGGTTTC TGACATCCGG CGGGTGACTC ACAACGGATC CAACAGACAT ATGGACTCGC 3') was synthesized and inserted by site directed mutagenesis into pBiCMV_NPL to generate create pBiCMV_NPiresL plasmid which will also be called Helper Plasmid Variant 1 (HPV1) (Seq ID No. 8). This plasmid is shown in FIG. 4A as Helper Plasmid 1

2.2.2 Synthesis of Helper Plasmid Variant 2

N protein sequence was amplified and subcloned in between the Nhe I and Xho I sites to obtain pIRES_N. P protein sequence was then amplified from pIRES_P and cloned into the Eco RI and Mlu I sites to create pIRES_NP. Finally, the L sequence was amplified from pIRES_L and cloned into pIRES_NP between the Sal I and Not I sites to obtain pIRES_NPL. In this form, this plasmid will express N and L proteins but not P. Therefore, a strategy based on the recently described 2A peptide vectors was used to promote the expression of P protein (szymczak and Vignali (2005)). The N and P open reading frames from pIRES_NPL were fused by inserting the oligonucleotide (5' ATCTTCTAGA CGGCTCCGGA GCCACGAACT TCTCTCTGTT AAAGCAAGCA GGAGACGTGG AAGAAAACCC CGGTCCCATG GCAGAAGAGC A 3') which encodes the porcine teschovirus 2Apeptide described by Szymczak et al (2007) flanked on the 5' end by the codons immediately before stop codon of MV N protein and on the 3' end by the first few codons of MV P protein by site directed mutagenesis to fuse the N and P protein regions into a single N2AP fusion protein and obtain pIRES_N2aPL plasmid which will also be called Helper Plasmid Variant 2 (HPV2) (Seq ID No. 9). This plasmid is shown in FIG. 4B as Helper Plasmid 2.

Figure 4A:
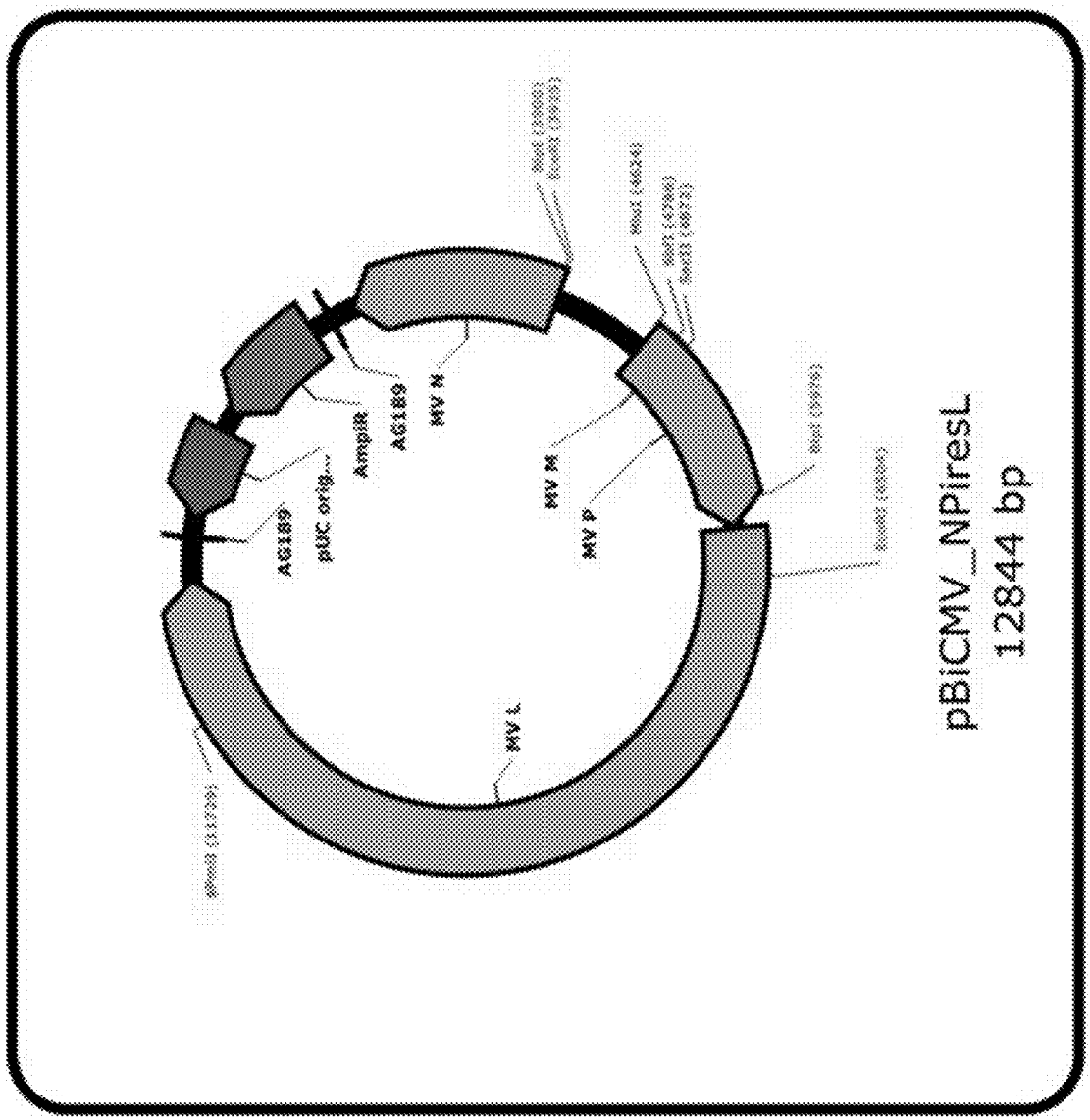
FIGS. 4A-4B: Schematic representations of the two variants of Helper plasmid created.
Figure 4B:
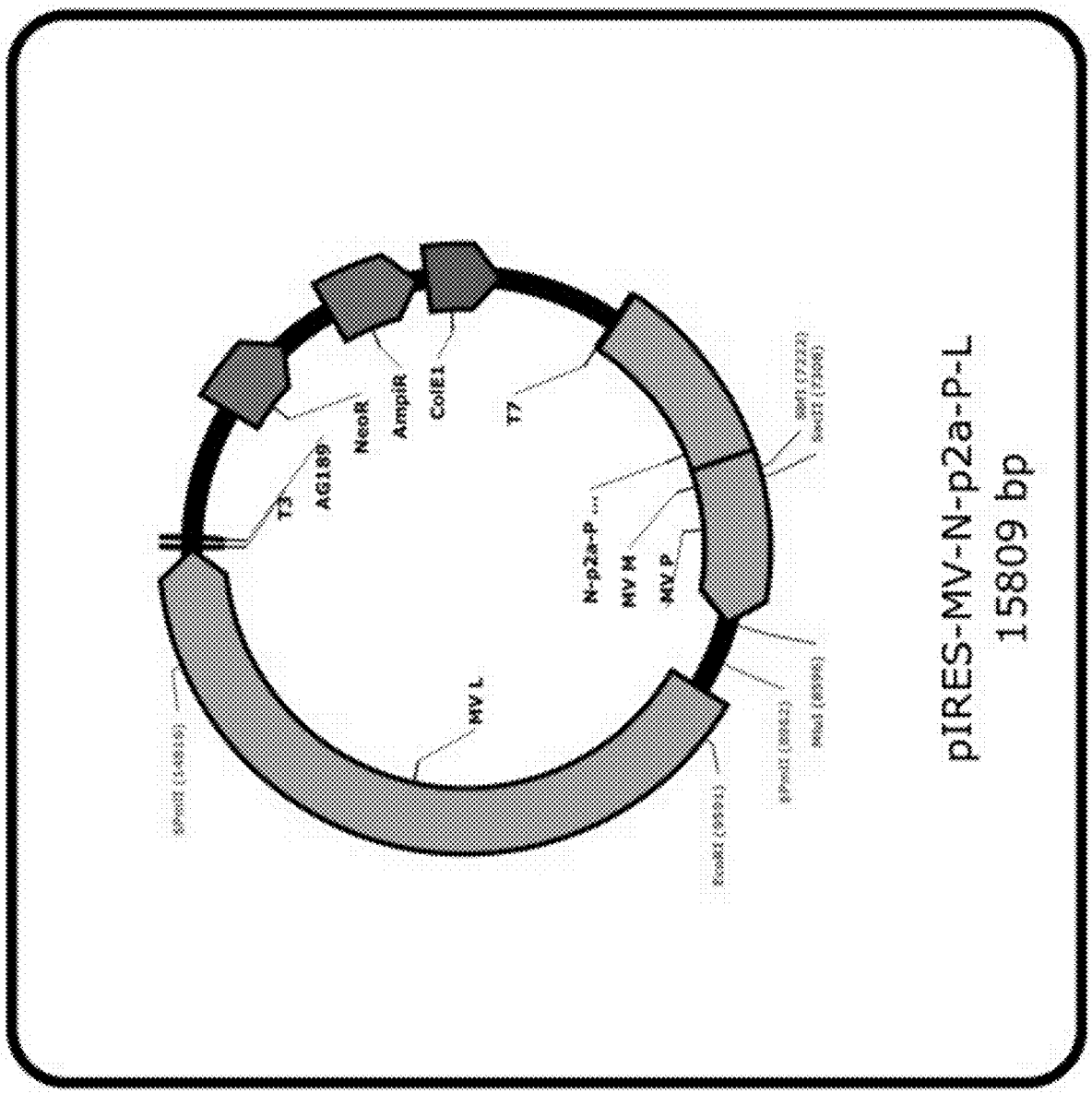

The plasmids HPV1 (pBiCMV_NPiresL) and HPV2 (pIRES_N2aPL) are represented schematically in FIGS. 4A-4B.

2.2.3 Synthesis of Equivalent Helper Plasmids Encoding N, P and L Proteins of Other Negative Stranded RNA Viruses The cloning strategy used for generation of these helper plasmids was then tested for its applicability to other negative stranded RNA viruses—mainly MV, Rinderpest (RPV), peste des petits ruminants (PPRV) canine distemper (CDV), newcastle disease (NDV) and sendai viruses (SeV). Coding regions of the nucleocapsid, phosphoprotein and large proteins were analysed for the presence of restriction enzymes Eco RI, Pst I, Nhe I, Eag I, Sal I, Xho I, Mlu I and Not I. Sites for Eco RI and Pst I were absent in the nucleocapsid proteins of MV and CDV. Similarly, sites for Nhe I and Xho I were absent in the nucleocapsid proteins of MV and SeV. However, variable number of sites for enzymes Eco RI, Pst I, Nhe I and Xho I were detected in the nucleocapsid of other viruses (Table 2).

TABLE 2

Presence of sites for Eco RI, Pst I, Nhe I and Xho I in the N protein of various negative stranded RNA viruses

| Virus | Gen bank No | Eco RI | Pst I | Nhe I | Xho I |
|---|---|---|---|---|---|
| MV | AY 486084.1 | 0 | 0 | 0 | 0 |
| RPV | AB 547190.1 | 1 | 3 | 1 | 0 |
| PPRV | HQ197753.1 | 0 | 2 | 0 | 1 |
| CDV | AB 687721.2 | 0 | 1 | 2 | 0 |
| NDV | HQ008337.1 | 0 | 0 | 1 | 2 |
| Sendai | NC_001552.1 | 0 | 1 | 0 | 0 |

Sites for enzymes Eag I, Sal I and Not I were absent from the L proteins of MV, PPRV, CDV and NDV. RPV and SeV contained 1 site for Sal I in their L proteins (Table 3).

TABLE 3

Presence of sites for Eag I, Sal I and Not I in the L proteins of various negative stranded RNA viruses

| Virus | Gen bank No | Eag I | Sal I | Not I |
|---|---|---|---|---|
| MV | AY 486084.1 | 0 | 0 | 0 |
| RPV | AB 547190.1 | 0 | 1 | 1 |
| PPRV | HQ197753.1 | 0 | 0 | 0 |
| CDV | AB 687721.2 | 0 | 0 | 0 |
| NDV | HQ008337.1 | 0 | 0 | 0 |
| Sendai | NC_001552.1 | 0 | 1 | 1 |

However, the genes for both these proteins encode a single protein each. Therefore, it would be easily possible to make synonymous mutations in their protein coding regions and eliminate the sites for these restriction enzymes. Therefore, the same cloning strategy can be easily used to clone the nucleocapsid and Large protein coding regions in a helper plasmid construct similar to either helper plasmid variant 1 or helper plasmid variant 2.

Similar to the above results, analysis of the phosphoprotein coding regions of these viruses revealed the presence of a variable number of sites for enzymes Nhe I, Eag I, Eco RI and Mlu I (Table 4). Sites for these enzymes were absent from the phosphoprotein coding regions of MV, CDV and NDV.

TABLE 3

Presence of sites for Nhe I, Eag I, Eco RI and Mlu I in the P of various negative stranded RNA viruses

| Virus | Gen bank No | Nhe I | Eag I | Eco RI | Mlu I |
|---|---|---|---|---|---|
| MV | AY 486084.1 | 0 | 0 | 0 | 0 |
| RPV | AB 547190.1 | 1 | 0 | 3 | 0 |
| RPV | Z30697.2 | 0 | 0 | 0 | 0 |
| PPRV | HQ197753.1 | 0 | 0 | 1 | 0 |
| CDV | AB 687721.2 | 0 | 0 | 0 | 0 |

TABLE 3-continued

Presence of sites for Nhe I, Eag I, Eco RI and Mlu I in the P of various negative stranded RNA viruses

| Virus | Gen bank No | Nhe I | Eag I | Eco RI | Mlu I |
|---|---|---|---|---|---|
| NDV | HQ008337.1 | 0 | 0 | 0 | 0 |
| Sendai | NC_001552.1 | 0 | 0 | 1 | 0 |

Although the P protein of RPV (AB547190) sequence is digested by Nhe I and Eco RI the regions corresponding to the recognition sites of these enzymes varies across different strains of RPV (e.g. Z30697.2 in Genbank). On the other hand, the Eco RI site in the P protein of PPRV appears to be highly conserved across most PPRV strains. However, this region of the P protein coding sequence does not overlap with the coding regions of C and V proteins which are also coded by the P gene transcript. Thus, it would be possible to introduce synonymous mutations in the P proteins of RPV and PPRV to enable the use of our proposed strategy for preparing the helper plasmids for MV, CDV, RPV, PPRV and NDV.

Therefore, the same restriction enzymes may be used to synthesize helper plasmid constructs equivalent to those described as Helper Plasmid Variant 1 and Helper Plasmid Variant 2 from the nucleoprotein (N or NP), phosphoprotein (P) and large (L) proteins of other negative stranded RNA viruses. Such variants will be useful as helper plasmids for reconstitution of corresponding viral RNA dependent RNA polymerase enzyme and its exploitation for protein or RNA expression and also generation of recombinant viruses as novel vaccines and/or therapeutic agents.

3. Expression of Recombinant Proteins by Plasmid Encoded RDRP

First the capacity of cloning plasmids to express RNA molecules which can serve as substrate for MV RNA dependent RNA polymerase (RDRP) was evaluated using a system similar to the one described by Martin et al, (2006). Briefly, Vero cells were transfected with Cloning plasmid, and individual plasmids expressing the N, P and L proteins of MV-E at a ratio of 1:1:1:0.5 in lipofectamine (Invitrogen) according to the manufacturer's protocol. Cells were incubated at 37° C. in 5% $CO_2$ for 48 hrs and evaluated for expression of green fluorescent protein (eGFP) by microscopy and fluorescence measurement using microplate reader.

In a subsequent experiment, Vero cells were transfected with equal proportions of one cloning plasmid (pUC-P1P-replicon-P1T or pIRES-HH-replicon-HDV or pIRES-P1P-replicon-P1T) and one helper plasmid (Helper variant 1 or Helper variant 2) in lipofectamine (Invitrogen) or xfect (Clonetech) and incubated at 37° C. in 5% $CO_2$ for 48 hrs and evaluated for the expression of green fluorescent protein (eGFP) by microscopy and fluorescence.

Figure 5A:
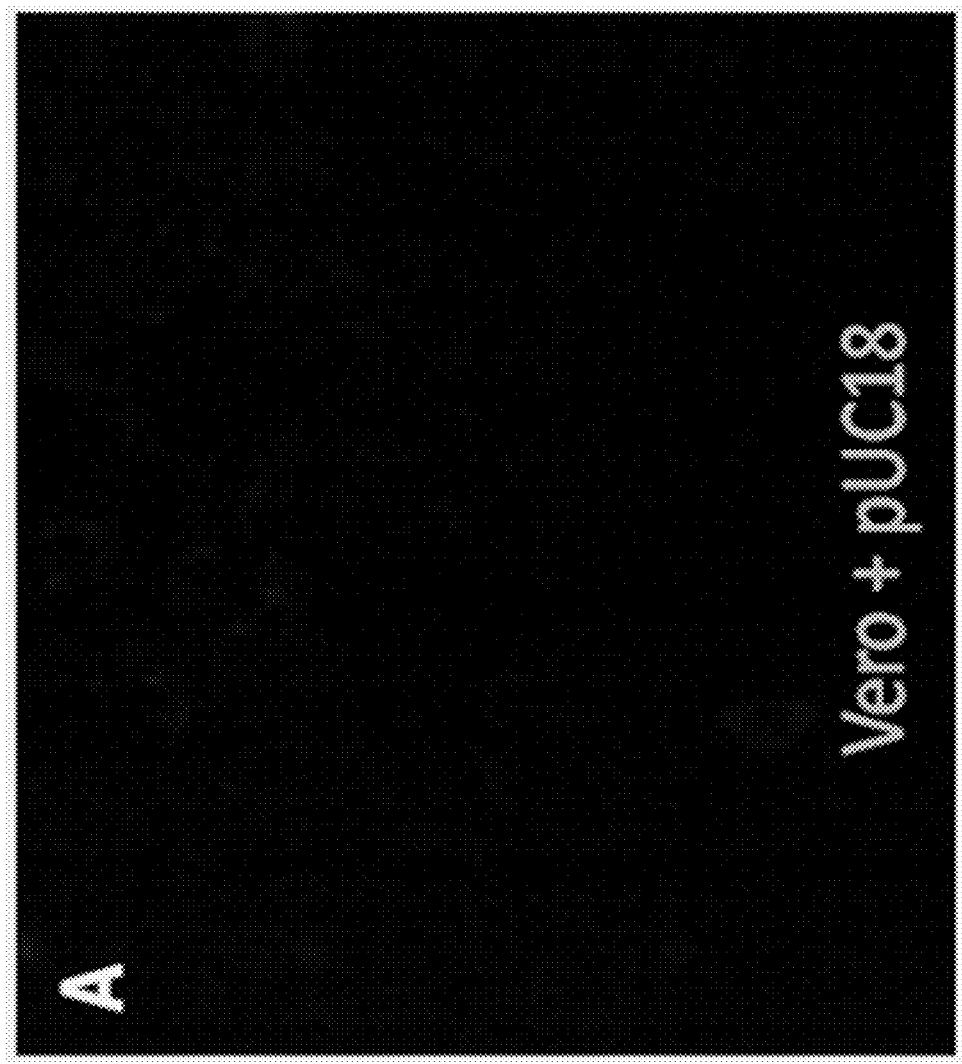
FIGS. 5A-5F.
Figure 5B:
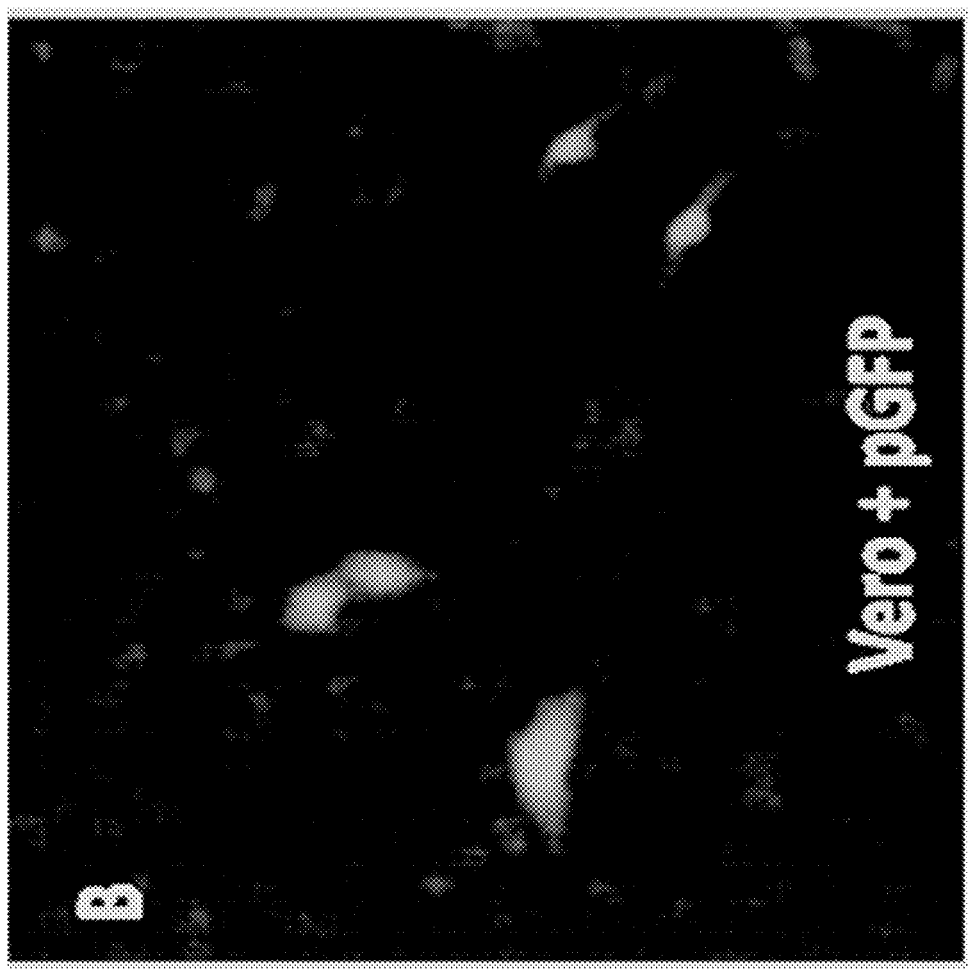
Figure 5C:
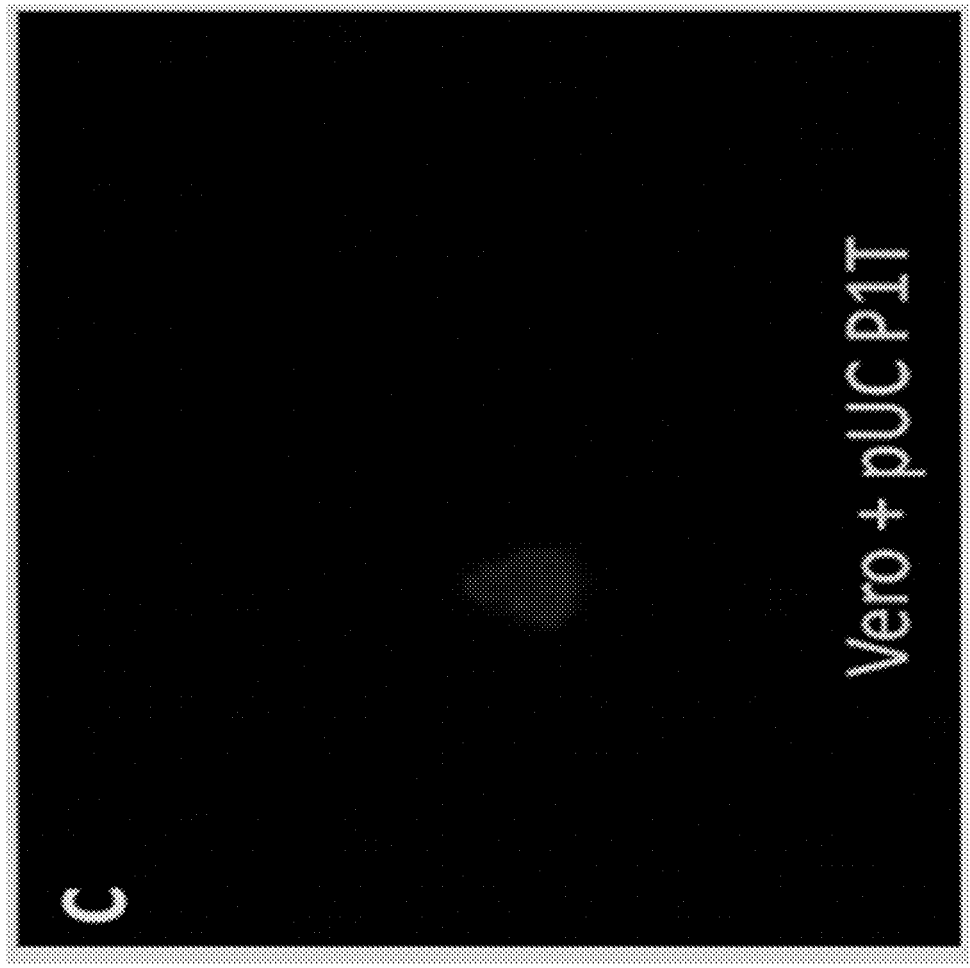
Figure 5D:
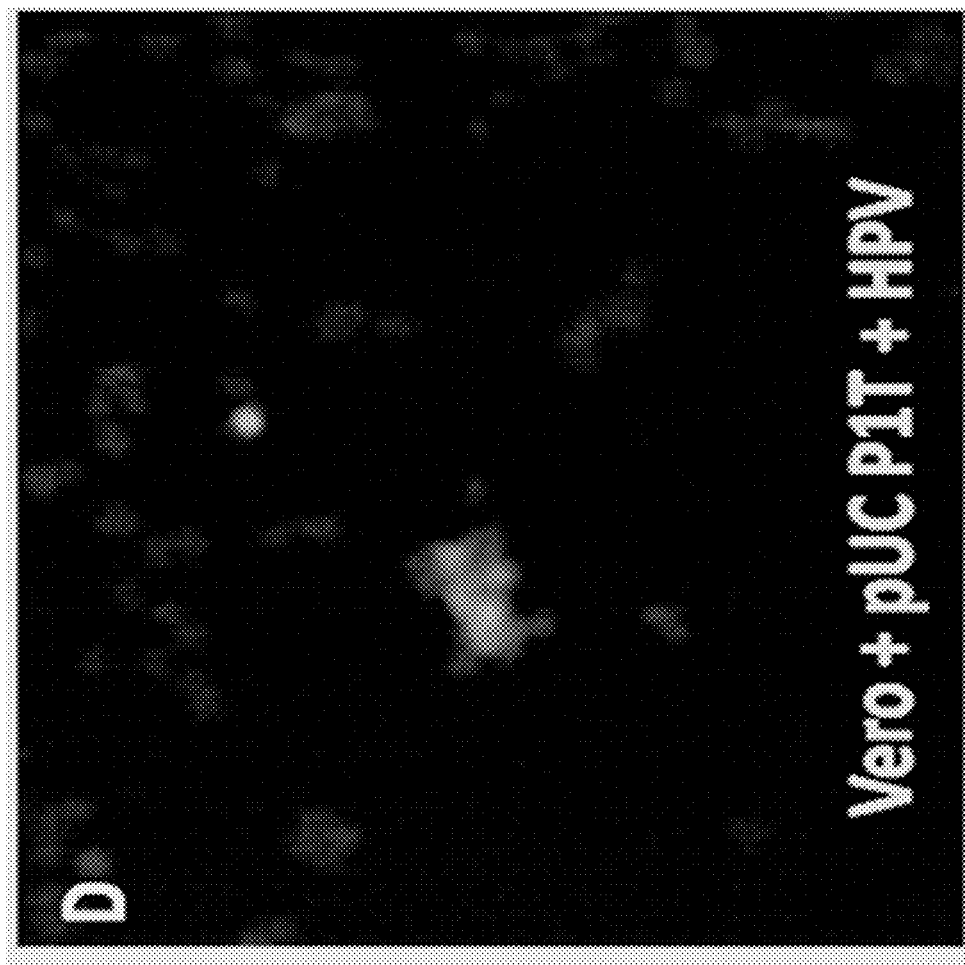
Figure 5E:
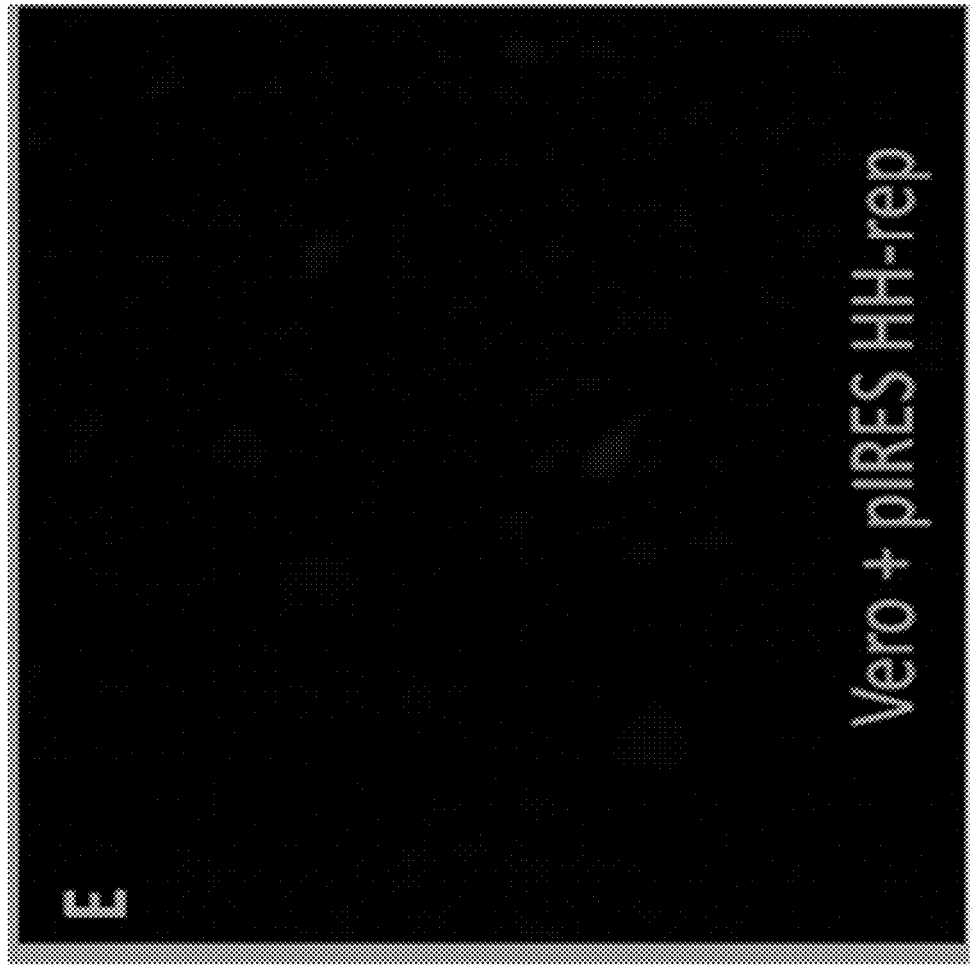
Figure 5F:

The results are shown in FIGS. 5A-5F. Briefly, Vero cells were co-transfected with Cloning plasmid encoding eGFP and HGH and Helper Plasmid Variant 1 (HPV 1) or Helper Plasmid Variant 2 (HPV 2), incubated for 48 hrs at 37° C. and observed for fluorescence and expression of HGH. FIG. 5A shows that transfection of control plasmid—pUC 18 alone—does not result in eGFP expression (Negative Control). FIG. 5B shows that transfection of a standard plasmid expressing eGFP leads to GFP expression (Positive control). FIG. 5C shows that transfection of Vero cells with Cloning Plasmid (pUC_P1P-replicon-P1T) alone does not result in the expression of eGFP. Similarly, transfection of Heper Plasmid (HPV) alone does not result in the expression of eGFP. In contrast, co-transfection of Cloning Plasmid along with the Helper Plasmid leads to the expression of eGFP (FIGS. 5D, 5E and 5F) indicating that GFP is expressed as a result of RdRP mediated expression.

4. Rescue of MV-E

The capacity of the helper plasmids to rescue MV-E from cDNA was tested. Plasmid pCDNA_MVgenome was cotransfected with Helper plasmid variant 1 or Helper plasmid variant 2 in Vero cells using Xfect and incubated overnight at 37° C. Transfection medium was replaced by fresh medium and cells were incubated further for two days. When syncytia involved 80% to 90% of cell layer, virus was harvested by scraping infected cells, freeze-thawing of cells and medium and centrifugation to remove cellular debris. Collected virus was titrated using the TCID50 titration method. Briefly, Vero cells were seeded into 96 well plate (7500 cells/well) and infected by serial 1:10 dilutions of virus sample in DMEM containing 5% DCS. After incubation at 37° C. for 7 days, cells were stained with crystal violet and virus dilution that resulted in infection of 50% of test unit was determined. The 50% end point described as tissue culture infectious dose (TCID50) was calculated by the Kaber method. Virus rescued from the pCDNA_MVgenome+Helper plasmid had titers of $10^6$ to $10^7$ TCID50/mL.

5. Rescue of Segmented MV-E using Plasmid Encoded RDRP

The capacity of the helper plasmids to rescue recombinant segmented MV-E from cDNA was tested. Vero cells were cotransfected with pCDNA_MVgenome, Cloning plasmid encoding eGFP and either HPV 1 or HPV 2 in equal proportions using Xfect and incubated overnight at 37° C. Transfection medium was replaced by fresh medium and continued to incubate with daily observation for syncytia formation. When syncytia involved 80% to 90% of cell layer, virus was harvested by scraping infected cells, freeze-thawing of cells and medium and centrifugation to remove cellular debris. Collected virus containing was titrated using the TCID50 titration method. Briefly, Vero cells were seeded into 96 well plate (7500 cells/well) and infected by serial 1:10 dilutions of virus sample in DMEM containing 5% DCS. After incubation at 37 C for 7 days, cells were stained with crystal violet and virus dilution that resulted in infection of 50% of test unit was determined. The 50% end point described as tissue culture infectious dose (TCID50) was calculated by the Kaber method. Virus rescued from the originally transfected cells had titers of $10^6$ to $10^7$ TCID50/mL.

Figure 6A:
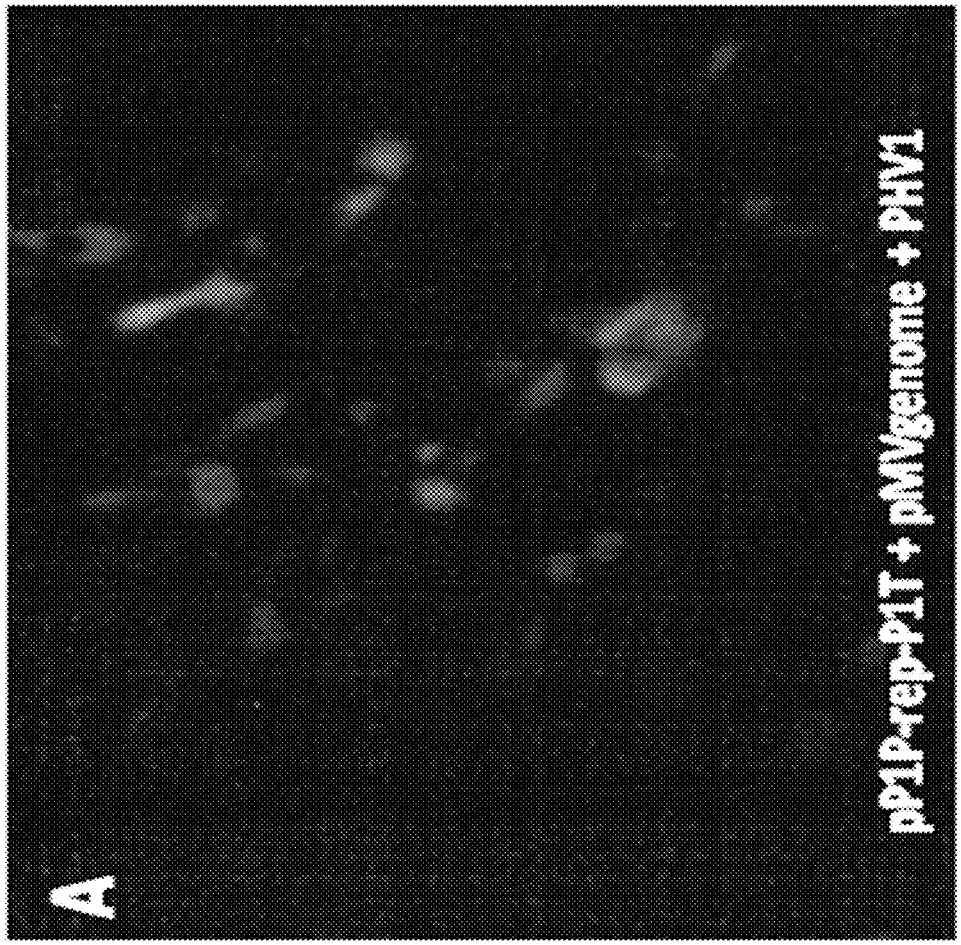
FIGS. 6A-6B: Rescue of segmented MV: Equal quantities of plasmids pCDNA_MVgenome, Cloning plasmid 1 (pIRES_HH-replicon-HDV) and HPV 1 were cotransfected into Vero cells using Xfect, incubated at 37° C. and observed daily for formation of syncytia. MV-E was harvested from the culture supernatant after syncytia formation covered>80%-90% and titrated using TCID50. Cells were observed simultaneously for expression of EGFP plasmid.
Figure 6B:
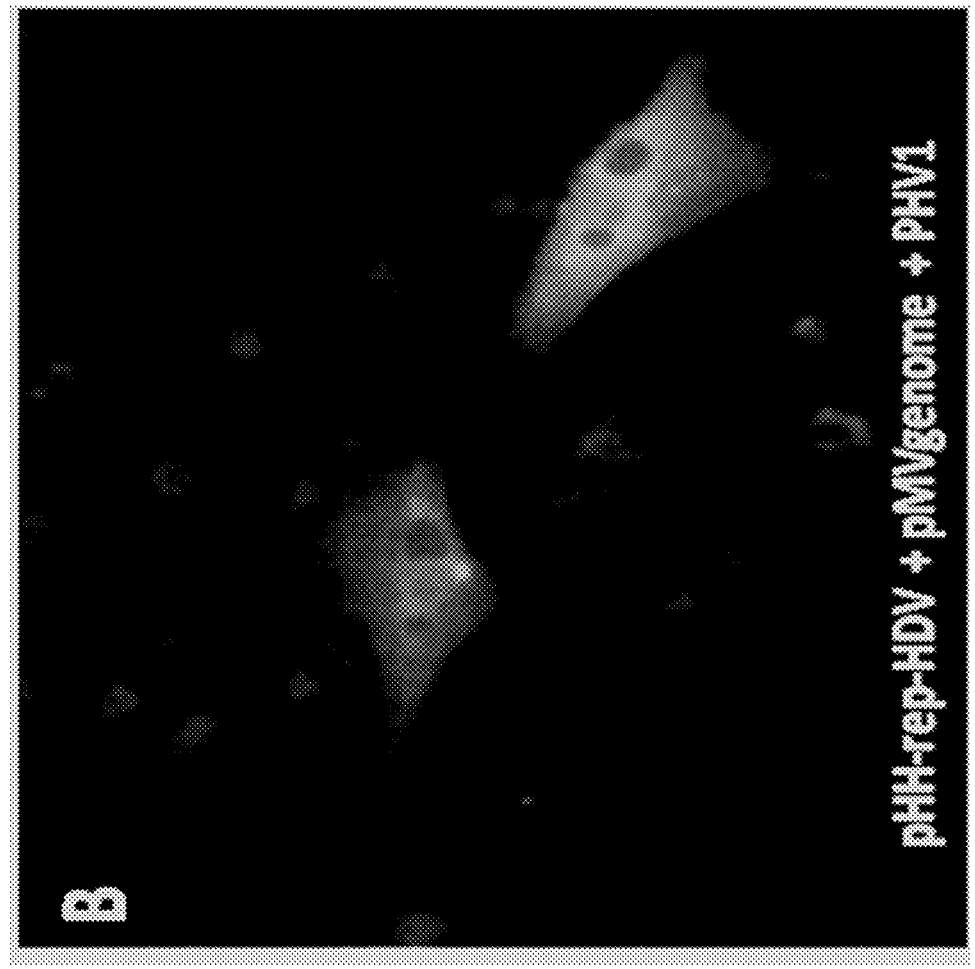

As shown in FIGS. 6A-6B, Cells infected with the virus harvested from the originally transfected vero cells also expressed eGFP indicating successful packaging eGFP encoding minireplicon along with MV-E genome into virions and its transfer to fresh cells.

I claim:

1. A method of producing non-segmented recombinant negative stranded RNA virus, said method comprising:
   a. obtaining a two plasmid system comprising:
      i. one cloning plasmid comprising a manipulatable replicon, wherein the manipulatable replicon is replaced by a cDNA fragment encoding the entire viral genomic RNA, said cDNA fragment is operatively linked to RNA polymerase (RNAp) I promoter; and
      ii. one helper plasmid comprising N, P, and L genes expressing the N, P, and L proteins respectively, wherein the N, P, and L genes are cloned into a single bi-cistronic DNA cassette containing a gene encoding fusion protein of N and P separated by a 2A peptide sequence, an IRES element, and a gene encoding L protein under the control of RNA polymerase (RNAp) II promoter;
   b. introducing the cloning plasmid and the helper plasmid into a host cell to produce a recombinant host cell; and
   c. producing non-segmented recombinant negative stranded RNA virus without the help of replicating helper vaccinia virus or exogenous RNA polymerase.

2. The method as claimed in claim 1, wherein said negative stranded RNA virus is selected from the group consisting of measles virus, Rinderpest virus, peste des petits ruminants virus, canine distemper virus, Newcastle disease virus, and sendai viruses.

3. The method as claimed in claim 2, wherein said negative stranded RNA virus is measles virus.

4. The method as claimed in claim 1, wherein said helper plasmid is selected from the group consisting of SEQ ID NO: 8, and SEQ ID NO: 9.

5. A method of producing recombinant measles virus, said method comprising:
   a. obtaining a two plasmid system comprising:
      i. one cloning plasmid comprising a manipulatable replicon, wherein the manipulatable replicon is replaced by a cDNA fragment encoding the entire measles virus genomic RNA, said cDNA fragment is operatively linked to RNA polymerase (RNAp) I promoter; and
      ii. one helper plasmid comprising N, P, and L genes expressing the N, P, and L proteins respectively, wherein the N, P, and L genes are cloned into a single bi-cistronic DNA cassette containing a gene encoding fusion protein of N and P separated by a 2A peptide sequence, an IRES element, and a gene encoding L protein under the control of RNA polymerase (RNAp) II promoter, said helper plasmid is selected from the group consisting of SEQ ID NO: 8, and SEQ ID NO: 9;
   b. introducing the cloning plasmid and the helper plasmid into a host cell to produce a recombinant host cell; and c. producing recombinant measles virus without the help of replicating helper vaccinia virus or exogenous RNA polymerase.

\* \* \* \* \*

SEQUENCE LISTING

<160> NUMBER OF SEQ ID NOS: 33

<210> SEQ ID NO 1
<211> LENGTH: 439

```
<212> TYPE: DNA
<213> ORGANISM: Artificial Sequence
<220> FEATURE:
<223> OTHER INFORMATION: Synthetic construct

<400> SEQUENCE: 1
accaaacaaa gttgggtaag gatagttcaa tcaatgatca ttttctagtg cacttaggat     60
tcaagatcct attatcaggg acaagagcag gattaaggat atccgagtcg cgacgcgtac    120
atgtagcgct cgcaccggtc cgcgggcgc gccctcgagg tgcgagaggc cgaggaccag     180
aacaacatcc gcctaccctc catcattgtt ataaaaaact taggaaccag gtccacacag    240
ccgccagccc atcaaccatc cactcccacg attggagccg cacgtgtcta gagggcccgt    300
ttaaaccctg caggttaatt aagtgaattc ttggttgaac tccggaaccc taatcctgcc    360
ctaggtggtt aggcattatt tgcaatagat taaagaaaac tttgaaaata cgaagtttct    420
attcccagct ttgtctggt                                                 439

<210> SEQ ID NO 2
<211> LENGTH: 614
<212> TYPE: DNA
<213> ORGANISM: Artificial Sequence
<220> FEATURE:
<223> OTHER INFORMATION: Synthetic construct

<400> SEQUENCE: 2
aagcttgcta gcaccaactt tgtttggtct gatgagtccg tgaggacgaa acccggagtc     60
ccgggtcacc aaacaaagtt gggtaaggat agttcaatca atgatcattt tctagtgcac    120
ttaggattca agatcctatt atcagggaca agagcaggat taaggatatc cgagtcgcga    180
cgcgtacatg tagcgctcgc accggtccgc ggggcgcgcc ggcgcgccct cgaggtgcga    240
gaggccgagg accagaacaa catccgccta ccctccatca ttgttataaa aaacttagga    300
accaggtcca cacagccgcc agcccatcaa ccatccactc ccacgattgg agccgcacgt    360
gtctagaggg cccgtttaaa ccctgcaggt ttaattaagt gaattcttgg ttgaactccg    420
gaaccctaat cctgccctag gtggttaggc attatttgca atagattaaa gaaactttg    480 aaaatacgaa gtttctattc ccagctttgt ctggtgccgg ccatggtccc agcctcctcg    540
ctggcggccg gtgggcaaca ttccgagggg accgtccct cggtaatggc gaatgggacc    600
gcggccgcga gctc                                                      614

<210> SEQ ID NO 3
<211> LENGTH: 969
<212> TYPE: DNA
<213> ORGANISM: Artificial Sequence
<220> FEATURE:
<223> OTHER INFORMATION: Synthetic construct

<400> SEQUENCE: 3
aagcttggct agcacatcct cttggtccta tcacggttat gaggtcgacc agttgttgct     60
ttgatgttcg gttctctcgt tgattgggac aatatttggg gcacttcgcc ggtcccgact    120
tccagaattt ccgtgtggtc tgtgaattta tcaccgctac actgtcatca tattccagtt    180
ttgcaatctg ctctctttgt acctgcagat aggtaccaaa caaagttggg taaggatagt    240
tcaatcaatg atcattttct agtgcactta ggattcaaga tcctattatc agggacaaga    300
gcaggattaa ggatatccga gtcgcgacgc gtacatgtag cgctcgcacc ggtccgcggg    360
gcgcgccctc gaggtgcgag aggccgagga ccagaacaac atccgcctac cctccatcat    420
```

| | |
|---|---:|
| tgttataaaa aacttaggaa ccaggtccac acagccgcca gcccatcaac catccactcc | 480 |
| cacgattgga gccgcacgtg tctagagggc ccgtttaaac cctgcaggtt taattaagtg | 540 |
| aattcttggt tgaactccgg aaccctaatc ctgccctagg tggttaggca ttatttgcaa | 600 |
| tagattaaag aaaactttga aaatacgaag tttctattcc cagctttgtc tggtttttt | 660 |
| cccccccaac ttcggaggtc gaccagtact ccgggcgaca ctttgttttt tttttttccc | 720 |
| ccgatgctgg aggtcgacca gatgtccgaa agtgtccccc ccccccccccc ccccccccg | 780 |
| gcgcggagcg gcgggccac cccggacccc tttttttttt tttttttttt ttttaaattc | 840 |
| ctggaacctt taggtcgacc agttgtccgt cttttactcc ttcatatagg tcgaccagta | 900 |
| ctccgggtgg tactttgtct ttttctgaaa atcccagagg tcgaccagat atccgcggcc | 960 |
| gccgagctc | 969 |

<210> SEQ ID NO 4
<211> LENGTH: 1690
<212> TYPE: DNA
<213> ORGANISM: Artificial Sequence
<220> FEATURE:
<223> OTHER INFORMATION: Synthetic construct

<400> SEQUENCE: 4

| | |
|---|---:|
| ggccgcttcc ctttagtgag ggttaatgct tcgagcagac atgataagat acattgatga | 60 |
| gtttggacaa accacaacta gaatgcagtg aaaaaaatgc tttatttgtg aaatttgtga | 120 |
| tgctattgct ttatttgtaa ccattataag ctgcaataaa caagttaaca acaacaattg | 180 |
| cattcatttt atgtttcagg ttcagggggga gatgtgggag gttttttaaa gcaagtaaaa | 240 |
| cctctacaaa tgtggtaaaa tccgataagg atcgatccgg gctggcgtaa tagcgaagag | 300 |
| gcccgcaccg atcgcccttc ccaacagttg cgcagcctga atggcgaatg gacgcgccct | 360 |
| gtagcggcgc attaagcgcg gcgggtgtgg tggttacgcg cagcgtgacc gctacacttg | 420 |
| ccagcgccct agcgcccgct cctttcgctt tcttcccttc ctttctcgcc acgttcgccg | 480 |
| gctttccccg tcaagctcta aatcgggggc tccctttagg gttccgattt agagctttac | 540 |
| ggcacctcga ccgcaaaaaa cttgatttgg gtgatggttc acgtagtggg ccatcgccct | 600 |
| gatagacggt ttttcgccct ttgacgttgg agtccacgtt ctttaatagt ggactcttgt | 660 |
| tccaaactgg aacaacactc aaccctatct cggtctattc ttttgattta agggattt | 720 |
| tgccgatttc ggcctattgg ttaaaaaatg agctgattta caaatatttt aacgcgaatt | 780 |
| ttaacaaaat attaacgttt acaatttcgc ctgatgcggt attttctcct tacgcatctg | 840 |
| tgcggtattt cacaccgcat acgcggatct gcgcagcacc atggcctgaa ataacctctg | 900 |
| aaagaggaac ttggttaggt accttctgag gcggaaagaa ccagctgtgg aatgtgtgtc | 960 |
| agttagggtg tggaaagtcc ccaggctccc cagcaggcag aagtatgcaa agcatgcatc | 1020 |
| tcaattagtc agcaaccagg tgtggaaagt ccccaggctc cccagcaggc agaagtatgc | 1080 |
| aaagcatgca tctcaattag tcagcaacca tagtcccgcc cctaactccg cccatcccgc | 1140 |
| ccctaactcc gcccagttcc gcccattctc cgccccatgg ctgactaatt ttttttattt | 1200 |
| atgcagaggc cgaggccgcc tcggcctctg agctattcca gaagtagtga ggaggctttt | 1260 |
| ttggaggcct aggcttttgc aaaaagcttg attcttctga cacaacagtc tcgaacttaa | 1320 |
| ggctagagcc accatgattg aacaagatgg attgcacgca ggttctccgg ccgcttgggt | 1380 |
| ggagaggcta ttcggctatg actgggcaca acagacaatc ggctgctctg atgccgccgt | 1440 |
| gttccggctg tcagcgcagg ggcgcccggt tctttttgtc aagaccgacc tgtccggtgc | 1500 |

| cctgaatgaa ctgcaggacg aggcagcgcg gctatcgtgg ctggccacga cgggcgttcc | 1560 |
| ttgcgcagct gtgctcgacg ttgtcactga agcgggaagg gactggctgc tattgggcga | 1620 |
| agtgccgggg caggatctcc tgtcatctca ccttgctcct gccgagaaag tatccatcat | 1680 |
| ggctgatgca | 1690 |

<210> SEQ ID NO 5
<211> LENGTH: 1690
<212> TYPE: DNA
<213> ORGANISM: Artificial Sequence
<220> FEATURE:
<223> OTHER INFORMATION: Synthetic construct

<400> SEQUENCE: 5

| ggccgcttcc ctttagtgag ggttaatgct tcgagcagac atgataagat acattgatga | 60 |
| gtttggacaa accacaacta gaatgcagtg aaaaaaatgc tttatttgtg aaatttgtga | 120 |
| tgctattgct ttatttgtaa ccattataag ctgcaataaa caagttaaca acaacaattg | 180 |
| cattcatttt atgtttcagg ttcaggggga gatgtgggag gtttttttaaa gcaagtaaaa | 240 |
| cctctacaaa tgtggtaaaa tccgataagg atcgatccgg gctggcgtaa tagcgaagag | 300 |
| gcccgcaccg atcgcccttc ccaacagttg cgcagcctga atggcgaatg gacgcgccct | 360 |
| gtagcggcgc attaagcgcg gcgggtgtgg tggttacgcg cagcgtgacc gctacacttg | 420 |
| ccagcgccct agcgcccgct cctttcgctt tcttcccttc ctttctcgcc acgttcgccg | 480 |
| gctttccccg tcaagctcta aatcgggggc tccctttagg gttccgattt agagctttac | 540 |
| ggcacctcga ccgcaaaaaa cttgatttgg gtgatggttc acgtagtggg ccatcgccct | 600 |
| gatagacggt ttttcgccct ttgacgttgg agtccacgtt ctttaatagt ggactcttgt | 660 |
| tccaaactgg aacaacactc aaccctatct cggtctattc ttttgattta agggatttt | 720 |
| tgccgatttc ggcctattgg ttaaaaaatg agctgattta acaaatattt aacgcgaatt | 780 |
| ttaacaaaat attaacgttt acaatttcgc ctgatgcggt attttctcct tacgcatctg | 840 |
| tgcggtattt cacaccgcat acgcggatct gcgcagcacc atggcctgaa ataacctctg | 900 |
| aaagaggaac ttggttaggt accttctgag gcggaaagaa ccagctgtgg aatgtgtgtc | 960 |
| agttagggtg tggaaagtcc ccaggctccc cagcaggcag aagtatgcaa agcatgcatc | 1020 |
| tcaattagtc agcaaccagg tgtggaaagt ccccaggctc cccagcaggc agaagtatgc | 1080 |
| aaagcatgca tctcaattag tcagcaacca tagtcccgcc cctaactccg cccatcccgc | 1140 |
| ccctaactcc gcccagttcc gcccattctc cgccccatgg ctgactaatt ttttttattt | 1200 |
| atgcagaggc cgaggccgcc tcggcctctg agctattcca gaagtagtga ggaggctttt | 1260 |
| ttggaggcct aggcttttgc aaaaagcttg attcttctga cacaacagtc tcgaacttaa | 1320 |
| ggctagagcc accatgattg aacaagatgg attgcacgca ggttctccgg ccgcttgggt | 1380 |
| ggagaggcta ttcggctatg actgggcaca acagacaatc ggctgctctg atgccgccgt | 1440 |
| gttccggctg tcagcgcagg ggcgcccggt tctttttgtc aagaccgacc tgtccggtgc | 1500 |
| cctgaatgaa ctgcaggacg aggcagcgcg gctatcgtgg ctggccacga cgggcgttcc | 1560 |
| ttgcgcagct gtgctcgacg ttgtcactga agcgggaagg gactggctgc tattgggcga | 1620 |
| agtgccgggg caggatctcc tgtcatctca ccttgctcct gccgagaaag tatccatcat | 1680 |
| ggctgatgca | 1690 |

<210> SEQ ID NO 6

<211> LENGTH: 1690
<212> TYPE: DNA
<213> ORGANISM: Artificial Sequence
<220> FEATURE:
<223> OTHER INFORMATION: Synthetic construct

<400> SEQUENCE: 6

| | | | | | |
|---|---|---|---|---|---|
| agcttggcgt | aatcatggtc | atagctgttt | cctgtgtgaa | attgttatcc | gctcacaatt | 60 |
| ccacacaaca | tacgagccgg | aagcataaag | tgtaaagcct | ggggtgccta | atgagtgagc | 120 |
| taactcacat | taattgcgtt | gcgctcactg | cccgctttcc | agtcgggaaa | cctgtcgtgc | 180 |
| cagctgcatt | aatgaatcgg | ccaacgcgcg | gggagaggcg | gtttgcgtat | tgggcgctct | 240 |
| tccgcttcct | cgctcactga | ctcgctgcgc | tcggtcgttc | ggctgcggcg | agcggtatca | 300 |
| gctcactcaa | aggcggtaat | acggttatcc | acagaatcag | gggataacgc | aggaaagaac | 360 |
| atgtgagcaa | aaggccagca | aaaggccagg | aaccgtaaaa | aggccgcgtt | gctggcgttt | 420 |
| ttccataggc | tccgcccccc | tgacgagcat | cacaaaaatc | gacgctcaag | tcagaggtgg | 480 |
| cgaaacccga | caggactata | aagataccag | gcgtttcccc | ctggaagctc | cctcgtgcgc | 540 |
| tctcctgttc | cgaccctgcc | gcttaccgga | tacctgtccg | cctttctccc | ttcgggaagc | 600 |
| gtggcgcttt | ctcatagctc | acgctgtagg | tatctcagtt | cggtgtaggt | cgttcgctcc | 660 |
| aagctgggct | gtgtgcacga | accccccgtt | cagcccgacc | gctgcgcctt | atccggtaac | 720 |
| tatcgtcttg | agtccaaccc | ggtaagacac | gacttatcgc | cactggcagc | agccactggt | 780 |
| aacaggatta | gcagagcgag | gtatgtaggc | ggtgctacag | agttcttgaa | gtggtggcct | 840 |
| aactacggct | acactagaag | aacagtattt | ggtatctgcg | ctctgctgaa | gccagttacc | 900 |
| ttcggaaaaa | gagttggtag | ctcttgatcc | ggcaaacaaa | ccaccgctgg | tagcggtggt | 960 |
| ttttttgttt | gcaagcagca | gattacgcgc | agaaaaaaag | gatctcaaga | agatcctttg | 1020 |
| atcttttcta | cggggtctga | cgctcagtgg | aacgaaaact | cacgttaagg | gattttggtc | 1080 |
| atgagattat | caaaaaggat | cttcacctag | atccttttaa | attaaaaatg | aagttttaaa | 1140 |
| tcaatctaaa | gtatatatga | gtaaacttgg | tctgacagtt | accaatgctt | aatcagtgag | 1200 |
| gcacctatct | cagcgatctg | tctatttcgt | tcatccatag | ttgcctgact | ccccgtcgtg | 1260 |
| tagataacta | cgatacggga | gggcttacca | tctggcccca | gtgctgcaat | gataccgcga | 1320 |
| gacccacgct | caccggctcc | agatttatca | gcaataaacc | agccagccgg | aagggccgag | 1380 |
| cgcagaagtg | gtcctgcaac | tttatccgcc | tccatccagt | ctattaattg | ttgccgggaa | 1440 |
| gctagagtaa | gtagttcgcc | agttaatagt | ttgcgcaacg | ttgttgccat | tgctacaggc | 1500 |
| atcgtggtgt | cacgctcgtc | gtttggtatg | gcttcattca | gctccggttc | ccaacgatca | 1560 |
| aggcgagtta | catgatcccc | catgttgtgc | aaaaaagcgg | ttagctcctt | cggtcctccg | 1620 |
| atcgttgtca | gaagtaagtt | ggccgcagtg | ttatcactca | tggttatggc | agcactgcat | 1680 |
| aattctctta | | | | | | 1690 |

<210> SEQ ID NO 7
<211> LENGTH: 1690
<212> TYPE: DNA
<213> ORGANISM: Artificial Sequence
<220> FEATURE:
<223> OTHER INFORMATION: Synthetic construct

<400> SEQUENCE: 7

| | | | | | |
|---|---|---|---|---|---|
| ctctctcgcg | cgtttcggtg | atgacggtga | aaacctctga | cacatgcagc | tcccggagac | 60 |
| ggtcacagct | tgtctgtaag | cggatgccgg | gagcagacaa | gcccgtcagg | gcgcgtcagc | 120 |

| | |
|---|---:|
| gggtgttggc gggtgtcggg gctggcttaa ctatgcggca tcagagcaga ttgtactgag | 180 |
| agtgcaccat atgcggtgtg aaataccgca cagatgcgta aggagaaaat accgcatcag | 240 |
| gcgccattcg ccattcaggc tgcgcaactg ttgggaaggg cgatcggtgc gggcctcttc | 300 |
| gctattacgc cagctggcga aggggggatg tgctgcaagg cgattaagtt gggtaacgcc | 360 |
| agggttttcc cagtcacgac gttgtaaaac gacggccagt gaattcaagc ttgctagcac | 420 |
| caactttgtt tggtctgatg agtccgtgag gacgaaaccc ggagtccgg gtcaccaaac | 480 |
| aaagttgggt aaggatagtt caatcaatga tcattttcta gtgcacttag gattcaagat | 540 |
| cctattatca gggacaagag caggattaag gatatccgag tcgcgacgcg tacatgtagc | 600 |
| gctcgcaccg gtccgcgggg cgcgccggcg cgccctcgag gtgcgagagg ccgaggacca | 660 |
| gaacaacatc cgcctaccct ccatcattgt tataaaaaac ttaggaacca ggtccacaca | 720 |
| gccgccagcc catcaaccat ccactcccac gattggagcc gcacgtgtct agagggcccg | 780 |
| tttaaaccct gcaggtttaa ttaagtgaat tcttggttga actccggaac cctaatcctg | 840 |
| ccctaggtgg ttaggcatta tttgcaatag attaaagaaa actttgaaaa tacgaagttt | 900 |
| ctattcccag ctttgtctgg tgccggccat ggtcccagcc tcctcgctgg cggccggtgg | 960 |
| gcaacattcc gaggggaccg tcccctcggt aatggcgaat gggaccgcgg ccgcgagctc | 1020 |
| aagcttggcg taatcatggt catagctgtt cctgtgtga aattgttatc cgctcacaat | 1080 |
| tccacacaac atacgagccg gaagcataaa gtgtaaagcc tggggtgcct aatgagtgag | 1140 |
| ctaactcaca ttaattgcgt tgcgctcact gcccgctttc cagtcgggaa acctgtcgtg | 1200 |
| ccagctgcat taatgaatcg gccaacgcgc ggggagaggc ggtttgcgta ttgggcgctc | 1260 |
| ttccgcttcc tcgctcactg actcgctgcg ctcggtcgtt cggctgcggc gagcggtatc | 1320 |
| agctcactca aaggcggtaa tacggttatc cacagaatca ggggataacg caggaaagaa | 1380 |
| catgtgagca aaaggccagc aaaaggccag gaaccgtaaa aaggccgcgt tgctggcgtt | 1440 |
| tttccatagg ctccgccccc ctgacgagca tcacaaaaat cgacgctcaa gtcagaggtg | 1500 |
| gcgaaacccg acaggactat aaagatacca ggcgtttccc cctggaagct ccctcgtgcg | 1560 |
| ctctcctgtt ccgaccctgc cgcttaccgg atacctgtcc gcctttctcc cttcgggaag | 1620 |
| cgtggcgctt tctcatagct cacgctgtag gtatctcagt tcggtgtagg tcgttcgctc | 1680 |
| caagctgggc | 1690 |

<210> SEQ ID NO 8
<211> LENGTH: 1690
<212> TYPE: DNA
<213> ORGANISM: Artificial Sequence
<220> FEATURE:
<223> OTHER INFORMATION: Synthetic construct

<400> SEQUENCE: 8

| | |
|---|---:|
| tcgacgatat ctccagagga tcataatcag ccataccaca tttgtagagg ttttacttgc | 60 |
| tttaaaaaac ctcccacacc tccccctgaa cctgaaacat aaaatgaatg caattgttgt | 120 |
| tgttaacttg tttattgcag cttataatgg ttacaaataa agcaatagca tcacaaattt | 180 |
| cacaaataaa gcatttttt cactgccccg agcttcctcg ctcactgact cgctgcgctc | 240 |
| ggtcgttcgg ctgcggcgag cggtatcagc tcactcaaag gcggtaatac ggttatccac | 300 |
| agaatcaggg gataacgcag gaaagaacat gtgagcaaaa ggccagcaaa aggccaggaa | 360 |
| ccgtaaaaag gccgcgttgc tggcgttttt ccataggctc cgcccccctg acgagcatca | 420 |

```
caaaaatcga cgctcaagtc agaggtggcg aaacccgaca ggactataaa gataccaggc      480
gtttccccct ggaagctccc tcgtgcgctc tcctgttccg accctgccgc ttaccggata      540
cctgtccgcc tttctccctt cgggaagcgt ggcgctttct caatgctcac gctgtaggta      600
tctcagttcg gtgtaggtcg ttcgctccaa gctgggctgt gtgcacgaac cccccgttca      660
gcccgaccgc tgcgccttat ccggtaacta tcgtcttgag tccaacccgg taagacacga      720
cttatcgcca ctggcagcag ccactggtaa caggattagc agagcgaggt atgtaggcgg      780
tgctacagag ttcttgaagt ggtggcctaa ctacggctac actagaagga cagtatttgg      840
tatctgcgct ctgctgaagc cagttacctt cggaaaaaga gttggtagct cttgatccgg      900
caaacaaacc accgctggta cggtggtttt tttgtttgc aagcagcaga ttacgcgcag      960
aaaaaaagga tctcaagaag atcctttgat cttttctacg gggtctgacg ctcagtggaa     1020
cgaaaactca cgttaaggga ttttggtcat gagattatca aaaaggatct tcacctagat     1080
cctttttaaat taaaaatgaa gttttaaatc aatctaaagt atatatgagt aaacttggtc     1140
tgacagttac caatgcttaa tcagtgaggc acctatctca gcgatctgtc tatttcgttc     1200
atccatagtt gcctgactcc ccgtcgtgta gataactacg atacgggagg gcttaccatc     1260
tggccccagt gctgcaatga taccgcgaga cccacgctca ccggctccag atttatcagc     1320
aataaaccag ccagccggaa gggccgagcg cagaagtggt cctgcaactt tatccgcctc     1380
catccagtct attaattgtt gccgggaagc tagagtaagt agttcgccag ttaatagttt     1440
gcgcaacgtt gttgccattg ctacaggcat cgtggtgtca cgctcgtcgt ttggtatggc     1500
ttcattcagc tccggttccc aacgatcaag gcgagttaca tgatccccca tgttgtgcaa     1560
aaaagcggtt agctccttcg gtcctccgat cgttgtcaga agtaagttgg ccgcagtgtt     1620
atcactcatg gttatggcag cactgcataa ttctcttact gtcatgccat ccgtaagatg     1680
cttttctgtg                                                            1690
```

<210> SEQ ID NO 9
<211> LENGTH: 1690
<212> TYPE: DNA
<213> ORGANISM: Artificial Sequence
<220> FEATURE:
<223> OTHER INFORMATION: Synthetic construct

<400> SEQUENCE: 9

```
gcttcccttt agtgagggtt aatgcttcga gcagacatga taagatacat tgatgagttt       60
ggacaaacca caactagaat gcagtgaaaa aaatgcttta tttgtgaaat ttgtgatgct      120
attgctttat ttgtaaccat tataagctgc aataaacaag ttaacaacaa caattgcatt      180
cattttatgt ttcaggttca gggggagatg tgggaggttt tttaaagcaa gtaaaacctc      240
tacaaatgtg gtaaaatccg ataaggatcg atccgggctg gcgtaatagc gaagaggccc      300
gcaccgatcg cccttcccaa cagttgcgca gcctgaatgg cgaatggacg cgccctgtag      360
cggcgcatta agcgcggcgg gtgtggtggt tacgcgcagc gtgaccgcta cacttgccag      420
cgccctagcg cccgctccct tcgctttctt cccttccttt ctcgccacgt tcgccggctt      480
tccccgtcaa gctctaaatc ggggctccc tttagggttc cgatttagag ctttacggca      540
cctcgaccgc aaaaaacttg atttgggtga tggttcacgt agtgggccat cgccctgata      600
gacggttttt cgccctttga cgttggagtc cacgttcttt aatagtggac tcttgttcca      660
aactggaaca cactcaacc ctatctcggt ctattctttt gatttataag ggattttgcc      720
gatttcggcc tattggttaa aaaatgagct gatttaacaa atatttaacg cgaattttaa      780
```

```
caaaatatta acgtttacaa tttcgcctga tgcggtattt tctccttacg catctgtgcg      840
gtatttcaca ccgcatacgc ggatctgcgc agcaccatgg cctgaaataa cctctgaaag      900
aggaacttgg ttaggtacct tctgaggcgg aaagaaccag ctgtggaatg tgtgtcagtt      960
agggtgtgga aagtccccag gctccccagc aggcagaagt atgcaaagca tgcatctcaa     1020
ttagtcagca accaggtgtg gaaagtcccc aggctcccca gcaggcagaa gtatgcaaag     1080
catgcatctc aattagtcag caaccatagt cccgccccta actccgccca tcccgcccct     1140
aactccgccc agttccgccc attctccgcc ccatggctga ctaatttttt ttatttatgc     1200
agaggccgag gccgcctcgg cctctgagct attccagaag tagtgaggag cttttttgg      1260 aggcctaggc ttttgcaaaa agcttgattc ttctgacaca acagtctcga acttaaggct     1320
agagccacca tgattgaaca agatggattg cacgcaggtt ctccggccgc ttgggtggag     1380
aggctattcg gctatgactg ggcacaacag acaatcggct gctctgatgc cgccgtgttc     1440
cggctgtcag cgcaggggcg cccggttctt tttgtcaaga ccgacctgtc cggtgccctg     1500
aatgaactgc aggacgaggc agcgcggcta tcgtggctgg ccacgacggg cgttccttgc     1560
gcagctgtgc tcgacgttgt cactgaagcg ggaagggact ggctgctatt gggcgaagtg     1620
ccggggcagg atctcctgtc atctcacctt gctcctgccg agaaagtatc catcatggct     1680
gatgcaatgc                                                             1690

<210> SEQ ID NO 10
<211> LENGTH: 15
<212> TYPE: DNA
<213> ORGANISM: Artificial Sequence
<220> FEATURE:
<223> OTHER INFORMATION: Synthetic sequence

<400> SEQUENCE: 10
gcggccgcac caaac                                                        15

<210> SEQ ID NO 11
<211> LENGTH: 15
<212> TYPE: DNA
<213> ORGANISM: Artificial Sequence
<220> FEATURE:
<223> OTHER INFORMATION: Synthetic sequence

<400> SEQUENCE: 11
cctgaccgcg gatgc                                                        15

<210> SEQ ID NO 12
<211> LENGTH: 15
<212> TYPE: DNA
<213> ORGANISM: Artificial Sequence
<220> FEATURE:
<223> OTHER INFORMATION: Synthetic sequence

<400> SEQUENCE: 12
acctcgcatc cgcgg                                                        15

<210> SEQ ID NO 13
<211> LENGTH: 22
<212> TYPE: DNA
<213> ORGANISM: Artificial Sequence
<220> FEATURE:
<223> OTHER INFORMATION: Synthetic sequence

<400> SEQUENCE: 13
```

```
cctccagagt aatcgattaa gg                                              22

<210> SEQ ID NO 14
<211> LENGTH: 23
<212> TYPE: DNA
<213> ORGANISM: Artificial Sequence
<220> FEATURE:
<223> OTHER INFORMATION: Synthetic sequence

<400> SEQUENCE: 14
aatcgattac tctggaggag cag                                             23

<210> SEQ ID NO 15
<211> LENGTH: 27
<212> TYPE: DNA
<213> ORGANISM: Artificial Sequence
<220> FEATURE:
<223> OTHER INFORMATION: Synthetic sequence

<400> SEQUENCE: 15
cttgcaccct aagttttaat taactac                                         27

<210> SEQ ID NO 16
<211> LENGTH: 26
<212> TYPE: DNA
<213> ORGANISM: Artificial Sequence
<220> FEATURE:
<223> OTHER INFORMATION: Synthetic sequence

<400> SEQUENCE: 16
gaacaatatc ggtagttaat taaaac                                          26

<210> SEQ ID NO 17
<211> LENGTH: 20
<212> TYPE: DNA
<213> ORGANISM: Artificial Sequence
<220> FEATURE:
<223> OTHER INFORMATION: Synthetic sequence

<400> SEQUENCE: 17
tgagggactc gagcatactc                                                 20

<210> SEQ ID NO 18
<211> LENGTH: 26
<212> TYPE: DNA
<213> ORGANISM: Artificial Sequence
<220> FEATURE:
<223> OTHER INFORMATION: Synthetic sequence

<400> SEQUENCE: 18
ataagatagt agccatcctg gagtat                                          26

<210> SEQ ID NO 19
<211> LENGTH: 18
<212> TYPE: DNA
<213> ORGANISM: Artificial Sequence
<220> FEATURE:
<223> OTHER INFORMATION: Synthetic sequence

<400> SEQUENCE: 19
gtagggccat gtgctggg                                                   18

<210> SEQ ID NO 20
<211> LENGTH: 23
<212> TYPE: DNA
<213> ORGANISM: Artificial Sequence
```

```
<220> FEATURE:
<223> OTHER INFORMATION: Synthetic sequence

<400> SEQUENCE: 20
catagccgta acaaaaaggg tac                                              23

<210> SEQ ID NO 21
<211> LENGTH: 22
<212> TYPE: DNA
<213> ORGANISM: Artificial Sequence
<220> FEATURE:
<223> OTHER INFORMATION: Synthetic sequence

<400> SEQUENCE: 21
gagcatcaag tgaaggacca tg                                               22

<210> SEQ ID NO 22
<211> LENGTH: 25
<212> TYPE: DNA
<213> ORGANISM: Artificial Sequence
<220> FEATURE:
<223> OTHER INFORMATION: Synthetic sequence

<400> SEQUENCE: 22
gcattgtggt attatagagc ctatc                                            25

<210> SEQ ID NO 23
<211> LENGTH: 22
<212> TYPE: DNA
<213> ORGANISM: Artificial Sequence
<220> FEATURE:
<223> OTHER INFORMATION: Synthetic sequence

<400> SEQUENCE: 23
cggtttaaac cagacaaagc tg                                               22

<210> SEQ ID NO 24
<211> LENGTH: 24
<212> TYPE: DNA
<213> ORGANISM: Artificial Sequence
<220> FEATURE:
<223> OTHER INFORMATION: Synthetic sequence

<400> SEQUENCE: 24
gctagcatgg ccacactttt aagg                                             24

<210> SEQ ID NO 25
<211> LENGTH: 23
<212> TYPE: DNA
<213> ORGANISM: Artificial Sequence
<220> FEATURE:
<223> OTHER INFORMATION: Synthetic sequence

<400> SEQUENCE: 25
gcggccgcct agtctagaag att                                              23

<210> SEQ ID NO 26
<211> LENGTH: 22
<212> TYPE: DNA
<213> ORGANISM: Artificial Sequence
<220> FEATURE:
<223> OTHER INFORMATION: Synthetic sequence

<400> SEQUENCE: 26
gctagcatgg cagaagagca gg                                               22
```

<210> SEQ ID NO 27
<211> LENGTH: 24
<212> TYPE: DNA
<213> ORGANISM: Artificial Sequence
<220> FEATURE:
<223> OTHER INFORMATION: Synthetic sequence

<400> SEQUENCE: 27
gcggccgcct acttcattat tatc                                              24

<210> SEQ ID NO 28
<211> LENGTH: 27
<212> TYPE: DNA
<213> ORGANISM: Artificial Sequence
<220> FEATURE:
<223> OTHER INFORMATION: Synthetic sequence

<400> SEQUENCE: 28
gctagcatgg actcgctatc tgtcaac                                           27

<210> SEQ ID NO 29
<211> LENGTH: 23
<212> TYPE: DNA
<213> ORGANISM: Artificial Sequence
<220> FEATURE:
<223> OTHER INFORMATION: Synthetic sequence

<400> SEQUENCE: 29
gcggccgctt agtccttaat cag                                               23

<210> SEQ ID NO 30
<211> LENGTH: 130
<212> TYPE: DNA
<213> ORGANISM: Artificial Sequence
<220> FEATURE:
<223> OTHER INFORMATION: Synthetic sequence

<400> SEQUENCE: 30
ggccgttctg acatccggcg ggtttctgac atccggcggg tttctgacat ccggcgggtt       60
tctgacatcc ggcgggtttc tgacatccgg cgggtgactc acaacggatc caacagacat     120
atggactcgc                                                             130

<210> SEQ ID NO 31
<211> LENGTH: 91
<212> TYPE: DNA
<213> ORGANISM: Artificial Sequence
<220> FEATURE:
<223> OTHER INFORMATION: Synthetic sequence

<400> SEQUENCE: 31
atcttctaga cggctccgga gccacgaact tctctctgtt aaagcaagca ggagacgtgg       60
aagaaaaccc cggtcccatg gcagaagagc a                                     91

<210> SEQ ID NO 32
<211> LENGTH: 1690
<212> TYPE: DNA
<213> ORGANISM: Artificial Sequence
<220> FEATURE:
<223> OTHER INFORMATION: Synthetic construct

<400> SEQUENCE: 32
ggccgcttcc ctttagtgag ggttaatgct tcgagcagac atgataagat acattgatga       60
gtttggacaa accacaacta gaatgcagtg aaaaaaatgc tttatttgtg aaatttgtga     120

```
tgctattgct ttatttgtaa ccattataag ctgcaataaa caagttaaca acaacaattg      180
cattcatttt atgtttcagg ttcaggggga gatgtgggag gttttttaaa gcaagtaaaa      240
cctctacaaa tgtggtaaaa tccgataagg atcgatccgg gctggcgtaa tagcgaagag      300
gcccgcaccg atcgcccttc ccaacagttg cgcagcctga atggcgaatg gacgcgccct      360
gtagcggcgc attaagcgcg gcgggtgtgg tggttacgcg cagcgtgacc gctacacttg      420
ccagcgccct agcgcccgct cctttcgctt tcttcccttc ctttctcgcc acgttcgccg      480
gctttccccg tcaagctcta atcgggggct ccctttaggg ttccgattt agagctttac       540 ggcacctcga ccgcaaaaaa cttgatttgg gtgatggttc acgtagtggg ccatcgccct      600
gatagacggt ttttcgccct ttgacgttgg agtccacgtt ctttaatagt ggactcttgt      660
tccaaactgg aacaacactc aaccctatct cggtctattc ttttgattta aagggatttt      720
tgccgatttc ggcctattgg ttaaaaaatg agctgattta caaatatttt aacgcgaatt      780
ttaacaaaat attaacgttt acaatttcgc ctgatgcggt attttctcct tacgcatctg      840
tgcggtattt cacaccgcat acgcggatct gcgcagcacc atggcctgaa ataacctctg      900
aaagaggaac ttggttaggt accttctgag gcggaaagaa ccagctgtgg aatgtgtgtc      960
agttagggtg tggaaagtcc ccaggctccc cagcaggcag aagtatgcaa agcatgcatc     1020
tcaattagtc agcaaccagg tgtggaaagt ccccaggctc cccagcaggc agaagtatgc     1080
aaagcatgca tctcaattag tcagcaacca tagtcccgcc cctaactccg cccatcccgc     1140
ccctaactcc gcccagttcc gcccattctc cgccccatgg ctgactaatt ttttttattt     1200
atgcagaggc cgaggccgcc tcggcctctg agctattcca gaagtagtga ggaggctttt     1260
ttggaggcct aggcttttgc aaaaagcttg attcttctga cacaacagtc tcgaacttaa     1320
ggctagagcc accatgattg aacaagatgg attgcacgca ggttctccgg ccgcttgggt     1380
ggagaggcta ttcggctatg actgggcaca acagacaatc ggctgctctg atgccgccgt     1440
gttccggctg tcagcgcagg ggcgcccggt tctttttgtc aagaccgacc tgtccggtgc     1500
cctgaatgaa ctgcaggacg aggcagcgcg gctatcgtgg ctggccacga cgggcgttcc     1560
ttgcgcagct gtgctcgacg ttgtcactga agcgggaagg gactggctgc tattgggcga     1620
agtgccgggg caggatctcc tgtcatctca ccttgctcct gccgagaaag tatccatcat     1680
ggctgatgca                                                            1690
```

<210> SEQ ID NO 33
<211> LENGTH: 1690
<212> TYPE: DNA
<213> ORGANISM: Artificial Sequence
<220> FEATURE:
<223> OTHER INFORMATION: Synthetic construct

<400> SEQUENCE: 33

```
gctagcacca actttgtttg gtctgatgag tccgtgagga cgaaacccgg agtcccgggt       60
caccaaacaa agttgggtaa ggatagttca atcaatgatc attttctagt gcacttagga      120
ttcaagatcc tattatcagg gacaagagca ggattaagga tatccgagtc gcgacgcgta      180
catgtagcgc tcgcaccggt ccgcggggcg cgccatggta gcaagggcg aggagctgtt       240 caccggggtg gtgcccatcc tggtcgagct ggacggcgac gtaaacggcc acaagttcag      300
cgtgtccggc gagggcgagg gcgatgccac ctacggcaag ctgaccctga agttcatctg      360
caccaccggc aagctgcccg tgccctggcc caccctcgtg accaccctga cctacggcgt      420
```

```
gcagtgcttc agccgctacc ccgaccacat gaagcagcac gacttcttca agtccgccat    480
gcccgaaggc tacgtccagg agcgcaccat cttcttcaag gacgacggca actacaagac    540
ccgcgccgag gtgaagttcg agggcgacac cctggtgaac cgcatcgagc tgaagggcat    600
cgacttcaag gaggacggca acatcctggg gcacaagctg gagtacaact acaacagcca    660
caacgtctat atcatggccg acaagcagaa gaacggcatc aaggtgaact tcaagatccg    720
ccacaacatc gaggacggca gcgtgcagct cgccgaccac taccagcaga acacccccat    780
cggcgacggc cccgtgctgc tgcccgacaa ccactacctg agcacccagt ccgccctgag    840
caaagacccc aacgagaagc gcgatcacat ggtcctgctg gagttcgtga ccgccgccgg    900
gatcactctc ggcatggacg agctgtacaa gtaaggcgcg ccctcgaggt gcgagaggcc    960
gaggaccaga acaacatccg cctaccctcc atcattgtta taaaaaactt aggaaccagg   1020
tccacacagc cgccagccca tcaaccatcc actcccacga ttggagccgc acgtgtctag   1080
agggcccgtt taaaccctgc aggttaatta attctgacat ccggcgggtt tctgacatcc   1140
ggcgggtttc tgacatccgg cgggtttctg acatccggcg ggtttctgac atccggcggg   1200
tgactcacaa ccccagaaac agacatatgg ctacaggctc ccggacgtcc ctgctcctgg   1260
cttttggcct gctctgcctg ccctggcttc aagagggcag tgccttccca accattccct   1320
tatccaggct ttttgacaac gctatgctcc gcgcccatcg tctgcaccag ctggcctttg   1380
acacctacca ggagtttgaa gaagcctata tcccaaagga acagaagtat tcattcctgc   1440 agaacccca gacctccctc tgtttctcag agtctattcc gacaccctcc aacagggagg   1500
aaacacaaca gaaatccaac ctagagctgc tccgcatctc cctgctgctc atccagtcgt   1560
ggctggagcc cgtgcagttc ctcaggagtg tcttcgccaa cagcctggtg tacggcgcct   1620
ctgacagcaa cgtctatgac ctcctaaagg acctagagga aggcatccaa acgctgatgg   1680
ggaggctgga                                                          1690
```